US009919004B2

(12) United States Patent
Kizhakkedathu et al.

(10) Patent No.: US 9,919,004 B2
(45) Date of Patent: Mar. 20, 2018

(54) POLYMER-BASED DIALYSATE

(71) Applicant: The University of British Columbia, Vancouver (CA)

(72) Inventors: Jayachandran Kizhakkedathu, New Westminster (CA); Caigan Du, Richmond (CA); Gerald Da Roza, West Vancouver (CA); Asher Mendelson, London (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 0 days.

(21) Appl. No.: 14/396,603

(22) PCT Filed: Apr. 18, 2013

(86) PCT No.: PCT/CA2013/000382
§ 371 (c)(1),
(2) Date: Oct. 23, 2014

(87) PCT Pub. No.: WO2013/159188
PCT Pub. Date: Oct. 31, 2013

(65) Prior Publication Data
US 2015/0141512 A1 May 21, 2015

Related U.S. Application Data

(60) Provisional application No. 61/637,716, filed on Apr. 24, 2012.

(51) Int. Cl.
*A61K 31/765* (2006.01)
*A61M 1/16* (2006.01)
*A61K 45/06* (2006.01)
*A61K 31/197* (2006.01)
*A61K 47/02* (2006.01)
*A61M 1/28* (2006.01)
*C08G 65/22* (2006.01)

(52) U.S. Cl.
CPC .......... *A61K 31/765* (2013.01); *A61K 31/197* (2013.01); *A61K 45/06* (2013.01); *A61K 47/02* (2013.01); *A61M 1/1654* (2013.01); *A61M 1/287* (2013.01); *C08G 65/22* (2013.01); *A61M 2202/0014* (2013.01); *A61M 2202/0498* (2013.01); *C08G 2340/00* (2013.01)

(58) Field of Classification Search
CPC .... A61K 31/197; A61K 31/765; A61K 45/06; A61K 47/02; A61M 1/1654; A61M 1/287; A61M 2202/0014; A61M 2202/0498; C08G 65/22; C08G 2340/00
See application file for complete search history.

(56) References Cited

U.S. PATENT DOCUMENTS

| | | | |
|---|---|---|---|
| 3,461,210 A | 8/1969 | Fossel | |
| 4,880,629 A | 11/1989 | Okamoto et al. | |
| 6,949,335 B2 * | 9/2005 | Fahy et al. | 435/1.1 |
| 2003/0202958 A1 * | 10/2003 | Strickland | A61K 31/765 424/78.38 |
| 2008/0292579 A1 * | 11/2008 | Brooks et al. | 424/78.37 |
| 2010/0324150 A1 | 12/2010 | Allard et al. | |

FOREIGN PATENT DOCUMENTS

| | | |
|---|---|---|
| CA | 2382864 A1 | 4/2001 |
| EP | 1891143 A1 | 2/2008 |
| WO | 03065801 A3 | 8/2003 |
| WO | 2006130978 A1 | 12/2006 |
| WO | 2008015015 A3 | 2/2008 |
| WO | 2008074154 | 6/2008 |
| WO | 2011106877 | 9/2011 |
| WO | 2012162789 | 12/2012 |

OTHER PUBLICATIONS

Baudette, P., et al., (2011) Anal. Chem. 83: 6500-6510.
Bleyer, A.J., et al., (1999) J. Am. Soc. Nephrol. 10(1): 154-159.
Calderon, M., et al., (2010) Adv. Mater. 22: 190-218.
Dernedde, J., et al., (2010) Proc. Nat. Acad. Sci., vol. 107, No. 46: 19679-19684.
Domenici, A., et al., (2011) Int. J Nephrol. 2011: 204216, 5 pages.
Gervais, M., et al., (2010) Macromolecules 43: 1778-1784.
Goldfarb-Rumyantzev, A.S., et al., (2005) Am. J. Kidney Dis. 46(3): 537-549.
Grassmann, A., et al., (2005) Nephrol. Dial. Transplant 20(12): 2587-2593.
International Search Report for Application No. PCT/CA2013/000382 dated Aug. 1, 2013.
Kainthan, R.K., et al., (2006) Biomacromolecules 7: 703-709.
Kainthan, R.K., et al., (2006) Biomaterials 27(31): 5377-5390.
Kainthan, R.K., et al., (2007) Biomaterials 28(31): 4581-4590.
Kainthan, R.K., et al., (2008) Biomaterials 29(11): 1693-1704.
Kizhakkedathu, J.N., et al., (2010) Biomacromolecules 11: 2567-2575.
Lang, S.M., et al., (2001) Perit. Dial. Int. 21(I): 52-58.
Marron, B., et al., (2008) Kidney Int. Suppl. 108: S42-S51.
Mendelson et al.: "Hyperbranched Glycerol is an Efficacious and Biocornpatible Novel Osmotic Agent in a Rodent Model of Peritoneal Dialysis"; Peritoneal Dialysis International, Jan. 2013, vol. 33, No. 1, pp. 15-27.
Nayak, K.S., et al., (2009),Contrib. Nephrol. 163: 270-277.
Rippe: "Hyperbranched Polyglycerol: A Future Alternative to Polyglucose in Peritoneal Dialysis Fluids?", Peritoneal Dialysis International, Jan. 2013, vol. 33, No. 1, pp. 5-7.
Rubin, H.R., et al., (2004) J. Am. Med. Assoc. 291(6):697-703.
Sezer, S., et al., (2011) Transplant Proc. 43(2): 485-487.
Sharif, A., Baboolal, K., (2011) Perit. Dial. Int., vol. 31, Suppl. 2: S58-S62.
Stiriba, S., et al., (2002) J. Am. Chem. Soc. 124: 9698-9699.
Theofilou, P., (2011) J Clin. Med. Res, 3(3): I32-I38.
Trespalacios, F.C., et al., (2003) Am. J Kidney Dis. 41 (6): 1267-1277.

(Continued)

*Primary Examiner* — Sudhakar Katakam
(74) *Attorney, Agent, or Firm* — Rudy J. Ng; Bozicevic, Field & Francis LLP

(57) ABSTRACT

Embodiments described herein provide a dialysate comprising a polyglycerol. The polyglycerol may be of a molecular weight between about 0.15 kDa and about 60 kDa. Also provided herein is the use of the dialysate as a diffusion agent and as an osmotic agent.

77 Claims, 15 Drawing Sheets

(56) References Cited

OTHER PUBLICATIONS

Turk, H., et al., (2004) Bioconjugate Chem. 15: 162-167.
Vonesh, E.F., et al., (2006) Kidney Int. Suppl. 103: S3-S11.
Wilms, D., et al., (2010) Acc. Chem. Res. 43: 129-141.
Yang, Q., et al., (2009) Clin. Nephrol. 72(1): 62-68.
European Seach Report for Application No. EP13780839 dated Sep. 25, 2015.
European Search Opinion for Application No. EP13780839 dated Sep. 25, 2015.
Lila et al. (2013) "Use of polyglycerol (PG), instead of polyethylene glycol (PEG), prevents induction of the accelerated blood clearance phenomenon against long-circulating liposomes upon repeated administration," International Journal of Pharmaceutics, 456: 235-242.
Class Monograph Haemodialysis Solutions, Health Canada, Oct. 9, 1996, 1-5.
Crawford-Bonadio & Diaz-Buxo (2004) "Comparison of Peritoneal Dialysis Solutions," Nephrology Nursing Journal, 31(5): 500-509 and 520.
European Pharmacopoeia 7.0, pp. 2695-2697 (2010, implemented Jan. 2011).
Heimburger & Blake (2007) "Apparatus for Peritoneal Dialysis," Handbook of Dialysis, 339-355, Lippincott Williams & Wilkins, Philadelphia USA.
Nagelschmidt et al., (1998) "Polyethylene Glycol 4000 Attenuates Adhesion Formation in Rats by Suppression of Peritoneal Inflammation and Collagen Incorporation," The American Journal of Surgery, 176: 76-80.
Rippe & Venturoli (2008)"Optimum Electroylte Composition of a Dialysis Solution," Peritoneal Dialysis International, 28 (3): S131-S136.
Ul-Haq et al., (2012) "Influence of architecture of high molecular weight linear and branched polyglycerols on their biocompatibility and biodistribution," Biomaterials, 33: 9135-9147.
Ul-Haq et al., (2014) "Hybrid Polyglycerols with Long Blood Circulation: Synthesis, Biocompatibility, and Biodistribution," Macromol. Biosci., 14: 1469-1482.
Davies et al., (2009) "The effects of low-sodium peritoneal dialysis fluids on blood pressure, thirst and volume status," Nephrol Dial Transplant, 24(5): 1609-1617.
De Graaff et al., (2010) "The Effects of a Dialysis Solution With A Combination of Glycerol/Amino Acids/Dextrose on The Peritoneal Membrane in Chronic Renal Failure," Peritoneal Dialysis International, 30(2) 192-200.
Du et al., (2014) "The size-dependent efficacy and biocompatibility of hyperbranched polyglycerol in peritoneal dialysis," Biomaterials, 35, 1378-1389.
Du et al., (2016) "Hyperbranched polyglycerol is superior to glucose for long-term preservation of peritoneal membrane in a rat model of chronic peritoneal dialysis," J Transl Med, 14:338 1-17.
European Best Practice Guideline working group on Peritoneal Dialysis, Peritoneal dialysis solutions, Nephrol Dial Transplant, 2005, 20 [Suppl 9], pp. ix16-ix20.
Fang et al., (2008) "Comparison Between Bicarbonate/Lactate and Standard Lactate Dialysis Solution in Peritoneal Transport and Ultrafiltration: A Prospective, Crossover Single-Dwell Study," Peritoneal Dialysis International, 28(1): 35-43.
Feriani et al., (1996) "Solutions for Peritoneal Dialysis," Replacement of Renal Function by Dialysis, 520-545 Kluwer Academic Publishers, Dordrecht, The Netherlands.
Feriani et al., (2004) "Solutions for peritoneal dialysis," Replacement of Renal Function by Dialysis, 505-537, Springer-Science+Business Media, B.V.
Garcia-Lopez et al., (2012) "An update on peritoneal dialysis solutions," Nature Reviews Nephrology, 8: 224-233.
Gault (1973) "Peritoneal dialysis solutions," C.M.A Journal, 108, 325-327.
Heaton et al., (1986) "Evaluation of glycerol as an osmotic agent for continuous ambulatory peritoneal dialysis in end-stage renal failure," Clinical Science, 70(1): 23-29.
Hoenich & Ronco, (2007) "Haemodialysis Fluid: Composition and Clinical Importance," Blood Purification, 25(1): 62-68.
McIntyre, (2007) "Update on peritoneal dialysis solutions," Kidney International, 71: 486-490.
Mortier et al., (2005) "Benefits of switching from a conventional to a low-GDP bicarbonate/lactate-buffered dialysis solution in a rat model," Kidney International, 67: 1559-1565.
Pajek et al., (2009) "Short-term effects of bicarbonate/lactate-buffered and conventional lactate-buffered dialysis solutions on peritoneal ultrafiltration: a comparative crossover study," Nephrol Dial Transplant, 24(5): 1617-1625.
Palmer, (1999) "Dialysate Composition in Hemodialysis and Peritoneal Dialysis, Atlas of Diseases of the Kidney, Philadelphia," Current Medicine, 2.1-2.8.
Petitclerc & Jacobs, (1995) "Dialysis sodium concentration: what is optimal and can it be individualized?" Nephrol Dial Transplant, 10(5): 596-599.
Schambye et al., (1992) "Bicarbonate versus Lactate-Based CAPD fluids: a Biocompatibility Study in Rabbits," Peritoneal Dialysis International, 12(3): 281-286.
Struijk & Krediet, (2000) "Sodium Balance in Automated Peritoneal Dialysis," Peritoneal Dialysis International, 20 (2), S101-S105.

* cited by examiner

POLYMER-BASED DIALYSATE

CROSS-REFERENCE TO RELATED APPLICATIONS

The present application is a national phase entry under 35 U.S.C. § 371 of International Application No. PCT/CA2013/000382 filed Apr. 18, 2013, published in English, which claims priority from U.S. Application 61/637,716 filed Apr. 24, 2012, all of which are incorporated herein by reference.

TECHNICAL FIELD

This invention relates to the polyglycerol field. In particular, the invention relates to osmotic and diffusion agents based on polyglycerols and their uses.

BACKGROUND

Numerous physiological functions involve the transport of water or solutes across a semi-permeable membrane. The driving force for such transport is a concentration gradient that exists across the membrane. Assuming that the pores of the membrane are large enough to accommodate the solutes, solutes will diffuse from a side of the membrane where the solute is more concentrated to a side of the membrane where the solute is less concentrated, in order to achieve a dynamic equilibrium. Diffusion is a type of passive transport as no energy is expended to make the process happen. Osmosis is a special case of passive transport in which water moves across a selectively permeable membrane from a hypotonic solution to a hypertonic solution. As both of these processes are dependent on the concentration of solutes, diffusion and osmosis may be controlled by adding a diffusion or osmotic agent to a system. Many treatments for conditions relating to, for example, electrolyte imbalances, acid-base imbalances, blood pressure, waste removal and build up of fluid involve removing solutes or water from a bodily fluid through the use of a diffusion agent and/or an osmotic agent, either in vivo or ex vivo, or involve using an osmotic agent to induce dehydration.

In cases where such imbalances arise as a result of reduced kidney function, patients have two options for renal replacement therapy, dialysis and kidney transplant. Two forms of dialysis are used in clinical practice: hemodialysis ("HD") and peritoneal dialysis ("PD"). PD may be used in conjunction with HD with rates of PD comprising 0-70% of Canadian national dialysis programs (Grassmann, A., et al., (2005) Nephrol. Dial. Transplant 20(12): 2587-2593). Epidemiological data has demonstrated non-inferior outcomes for PD patients compared to their hospital-based HD counterparts (Vonesh, E. F., et al., (2006) Kidney Int. Suppl. 103: S3-S11).

HD uses an external apparatus to clean a patient's blood through a vascular circuit, while PD uses the patient's own abdominal lining, the peritoneal membrane, as a filter for waste excretion. HD is usually performed in a dialysis facility three times per week for three to four hours, where trained nurses and technicians carry out the prescribed treatment using a dialysis machine under the direction of a physician. After receiving training by dialysis facility staff, patients administer PD multiple times daily at home, which allows them to live more independently; however, PD requires the regular upkeep and maintenance of an indwelling PD catheter and supplies. This increased autonomy has translated into increased quality-of-life and therapy satisfaction scores for PD patients when compared to HD patients (Theofilou, P. (2011) J. Clin. Med. Res. 3(3): 132-138; Rubin, H. R., et al., (2004) J. Am. Med. Assoc. 291(6):697-703). PD has also been shown to be less expensive than HD on the order of tens of thousands of dollars per patient-year (Sharif, A., Baboolal, K., (2011) Perit. Dial. Int. Suppl. 2: S58-S62), and has therefore gained increasing preference in developing countries with limited healthcare budget, healthcare infrastructure, and access to health services (Nayak, K. S., et al., (2009) Contrib. Nephrol. 163: 270-277).

In addition, many studies have demonstrated better preserved residual renal function in PD patients (Marron, B., et al., (2008) Kidney Int. Suppl. 108: S42-S51; Lang, S. M., et al., (2001) Petit. Dial. Int. 21(1): 52-57). This directly translates into better handling of phosphate, salt and fluid and results in less dietary restrictions and improved quality-of-life for PD patients (Marron, B., et al., (2008) Kidney Int. Suppl. 108: S42-S51). Patients also demonstrate reduced incidence of anemia and left ventricular hypertrophy (Marron, B., et al., (2008) Kidney Int. Suppl. 108: S42-S51). This may explain why the incidence of heart failure hospitalization is reduced in PD patients compared with matched HD counterparts (Trespalacios, F. C., et al., (2003) Am. J. Kidney Dis. 41(6): 1267-1277).

Moreover, there is increasing evidence that PD is a more suitable bridge to renal transplantation than HD for patients with end-stage renal disease. Patients on PD may have lower incidences of hepatitis infection and thus fewer complications with subsequent immunosuppressive therapy (Yang, Q., et al., (2009) Clin. Nephrol. 72(1): 62-68). Graft outcomes appear to be improved with PD patients compared to matched HD controls that undergo renal transplant (Sezer, S., et al., (2011) Transplant Proc. 43(2): 485-487; Domenici, A., et al., (2011) Int. J. Nephrol. 2011: 204216; Bleyer, A. J., et al., (1999) J. Am. Soc. Nephrol. 10(1): 154-159; Goldfarb-Rumyantzev, A. S., et al., (2005) Am. J. Kidney Dis. 46(3): 537-549). Patients on PD will also have preserved vascular access for future dialysis in the event of graft failure. Therefore, there is incentive to initiate PD first and attempt to offer PD as the exclusive pre-transplant dialysis modality for adult and pediatric patients awaiting timely renal transplant.

Current PD solutions may be prepared using a high concentration of glucose as a primary osmotic agent. This glucose may produce systemic and locoregional health complications for PD patients. Daily exposure to glucose can cause hyperglycemia, hyperinsulinemia, obesity and exacerbation of diabetes. Moreover, exposure to glucose and glucose degradation products has been shown to directly damage the peritoneal membrane leading to abnormal mesothelial transformation, maladaptive angiogenesis and ultrafiltration failure (UFF). This phenomenon is characterized clinically by increased membrane permeability to small solutes, rapid absorption of intraperitoneal glucose, and inadequate fluid removal during PD. UFF, and thus inadequate fluid removal with PD, is one of the main reasons patients will stop PD and require transition to HD. Furthermore, the use of glucose may be associated with increasing the susceptibility of PD patients to the development of peritonitis, the decline of residual kidney function, and the loss of peritoneal membrane function. Reducing peritoneal inflammation is likely to delay UFF and prolong the time patients spend on PD. Minimizing glucose exposure may prevent some of the metabolic complications associated with PD. Improving locoregional host defense and reducing the glucose concentration in the peritoneum may also lead to decreased rates of aseptic and bacterial peritonitis.

Icodextrin, a large glucose-based polymer, has been designed to mitigate many of the problems encountered with long-term glucose exposure. Indeed, clinical trials have shown improved metabolic parameters in patients prescribed PD regimens containing icodextrin despite the elevated levels of blood maltose seen with icodextrin therapy. Notably, cell count in the peritoneal effluent of PD patients is significantly higher with icodextrin than glucose, indicating the potential ongoing role of icodextrin in peritoneal inflammation. The main clinical role of icodextrin has been in patients with established UFF when glucose can no longer remove water from the body. Due to its large size, icodextrin will remain intraperitoneal for longer and therefore achieve more reliable ultrafiltration compared to glucose. Yet, icodextrin exists in the dialysis solution as a polydispersed molecule of varying molecular weights and loses osmotic efficiency compared to the same concentration of monodispersed polymer. Moreover, due to the relatively slow fluid kinetics of icodextrin, it can only be used once daily for an extended dwell. There still appears to be a need for alternative biocompatible PD solutions that can be used for multiple dwells per day.

The pH of the PD solution may also play a role in the biocompatibility of the PD solution. PD solutions having a physiological pH may prevent the peritoneal inflammation that eventually leads to peritoneal membrane failure. Conventional PD solutions are typically acidic. Therefore, developing a PD solution with a physiological pH may prolong the viability of the peritoneal membrane.

SUMMARY

The present application is based, in part, on the discovery that the polyglycerols described herein have surprising ultrafiltration capacity, waste removal properties, or solute clearance properties, and/or do not show peritoneal membrane injury (i.e. fibrosis, angiogenesis, encapsulating peritoneal sclerosis, and resulting ultrafiltration failure (UFF)) to the same degree or at all when compared to commonly used peritoneal dialysis (PD) solutions. Furthermore, the application is based, in part, on the discovery that the polyglycerols described herein show surprisingly good cell viability properties as compared to commonly used PD solutions.

Embodiments described herein provide non-glucose based dialysates having surprising ultrafiltration capacity. Embodiments described herein provide non-glucose based dialysates having surprising waste removal properties. Embodiments described herein provide non-glucose based dialysates having surprising solute clearance properties. Embodiments described herein provide non-glucose based dialysates show surprisingly no peritoneal membrane injury (i.e. fibrosis, angiogenesis, encapsulating peritoneal sclerosis, and resulting ultrafiltration failure (UFF)). Embodiments described herein provide non-glucose based dialysates show surprisingly minimal peritoneal membrane injury (i.e. fibrosis, angiogenesis, encapsulating peritoneal sclerosis, and resulting ultrafiltration failure (UFF)). Embodiments described herein provide non-glucose based dialysates having surprisingly good cell viability properties.

In one aspect, the present invention provides a dialysate comprising a polyglycerol wherein the polyglycerol is of a molecular weight between about 0.15 kDa and about 60 kDa. In a further embodiment, the molecular weight of the polyglycerol is between about 0.16 kDa and about 59 kDa, about 0.17 kDa and about 58 kDa, about 0.18 kDa and about 57 kDa, about 0.19 kDa and about 56 kDa, about 0.20 kDa and about 55 kDa, about 0.21 kDa and about 54 kDa, about 0.22 kDa and about 53 kDa, about 0.23 kDa and about 52 kDa, about 0.24 kDa and about 51 kDa, about 0.25 kDa and about 50 kDa, about 0.26 kDa and about 49 kDa, about 0.27 kDa and about 48 kDa, about 0.28 kDa and about 47 kDa, about 0.29 kDa and about 46 kDa, about 0.30 kDa and about 45 kDa, about 0.31 kDa and about 44 kDa, about 0.32 kDa and about 43 kDa, about 0.33 kDa and about 42 kDa, about 0.34 kDa and about 41 kDa, about 0.35 kDa and about 40 kDa, about 0.36 kDa and about 39 kDa, about 0.37 kDa and about 38 kDa, about 0.38 kDa and about 37 kDa, about 0.39 kDa and about 36 kDa, about 0.40 kDa and about 35 kDa, about 0.41 kDa and about 34 kDa, about 0.42 kDa and about 33 kDa, about 0.43 kDa and about 32 kDa, about 0.44 kDa and about 31 kDa, about 0.45 kDa and about 30 kDa, about 0.46 kDa and about 29 kDa, about 0.47 kDa and about 28 kDa, about 0.48 kDa and about 27 kDa, about 0.49 kDa and about 26 kDa, about 0.50 kDa and about 25 kDa, about 0.50 kDa and about 24 kDa, about 0.50 kDa and about 23 kDa, about 0.50 kDa and about 22 kDa, about 0.50 kDa and about 21 kDa, about 0.50 kDa and about 20 kDa, about 0.50 kDa and about 19 kDa, about 0.50 kDa and about 18 kDa, about 0.50 kDa and about 17 kDa, about 0.50 kDa and about 16 kDa, about 0.50 kDa and about 15 kDa, about 0.50 kDa and about 14 kDa, about 0.50 kDa and about 13 kDa, about 0.50 kDa and about 12 kDa, about 0.50 kDa and about 11 kDa, about 0.50 kDa and about 10 kDa, about 0.50 kDa and about 9 kDa, about 0.50 kDa and about 8 kDa, about 0.50 kDa and about 7 kDa, about 0.50 kDa and about 6 kDa, about 0.50 kDa and about 5 kDa, about 0.50 kDa and about 4 kDa, or about 0.50 kDa and about 3 kDa.

In another embodiment, the pH of the dialysate is between about 2.0 and about 9.0, about 2.1 and about 8.9, about 2.2 and about 8.8, about 2.3 and about 8.7, about 2.4 and about 8.6, about 2.5 and about 8.5, about 2.6 and about 8.4, about 2.7 and about 8.3, about 2.8 and about 8.2, about 2.9 and about 8.1, about 3.0 and about 8.0, about 3.1 and about 8.0, about 3.2 and about 8.0, about 3.3 and about 8.0, about 3.4 and about 8.0, about 3.5 and about 8.0, about 3.6 and about 8.0, about 3.7 and about 8.0, about 3.8 and about 8.0, about 3.9 and about 8.0, about 4.0 and about 8.0, about 4.1 and about 8.0, about 4.2 and about 8.0, about 4.3 and about 8.0, 4.4 and about 8.0, 4.5 and about 7.9, about 4.6 and about 7.9, about 4.7 and about 7.9, about 4.8 and about 7.9, about 4.9 and about 7.9, about 5.0 and about 7.9, about 5.1 and about 7.9, about 5.2 and about 7.8, about 5.3 and about 7.8, about 5.4 and about 7.8, about 5.5 and about 7.8, about 5.6 and about 7.7, about 5.7 and about 7.7, about 5.8 and about 7.7, about 5.9 and about 7.7, about 6.0 and about 7.6, about 6.1 and about 7.6, about 6.2 and about 7.6, about 6.3 and about 7.6, about 6.4 and about 7.6, or about 6.5 and about 7.5.

In another embodiment, the dialysate is in aqueous solution. In one embodiment, the polyglycerol comprises about 0.01% by weight to about 50% by weight of the dialysate solution, about 0.02% by weight to about 49% by weight of the dialysate solution, about 0.04% by weight to about 48% by weight of the dialysate solution, about 0.06% by weight to about 47% by weight of the dialysate solution, about 0.08% by weight to about 46% by weight of the dialysate solution, about 0.10% by weight to about 45% by weight of the dialysate solution, about 0.12% by weight to about 44% by weight of the dialysate solution, about 0.14% by weight to about 43% by weight of the dialysate solution, about 0.16% by weight to about 42% by weight of the dialysate solution, about 0.18% by weight to about 41% by weight of the dialysate solution, about 0.20% by weight to about 40% by weight of the dialysate solution, about 0.22% by weight to about 39% by weight of the dialysate solution, about 0.24% by weight to about 38% by weight of the dialysate solution, about 0.26% by weight to about 37% by weight of the dialysate solution, about 0.28% by weight to about 36% by weight of the dialysate solution, about 0.30% by weight to about 35% by weight of the dialysate solution, about 0.32% by weight to about 34% by weight of the dialysate solution, about 0.34% by weight to about 33% by weight of the dialysate solution, about 0.36% by weight to about 32% by weight of the dialysate solution, about 0.38% by weight to about 31% by weight of the dialysate solution, about 0.40% by weight to about 30% by weight of the dialysate solution, about 0.40% by weight to about 29% by weight of the dialysate solution, about 0.42% by weight to about 28% by weight of the dialysate solution, about 0.44% by weight to about 27% by weight of the dialysate solution, about 0.46% by weight to about 26% by weight of the dialysate solution, about 0.48% by weight to about 25% by weight of the dialysate solution, about 0.50% by weight to about 25% by weight of the dialysate solution, about 0.52% by weight to about 25% by weight of the dialysate solution, about 0.54% by weight to about 25% by weight of the dialysate solution, about 0.56% by weight to about 25% by weight of the dialysate solution, about 0.58% by weight to about 25% by weight of the dialysate solution, about 0.60% by weight to about 25% by weight of the dialysate solution, about 0.62% by weight to about 25% by weight of the dialysate solution, about 0.64% by weight to about 25% by weight of the dialysate solution, about 0.66% by weight to about 25% by weight of the dialysate solution, about 0.68% by weight to about 25% by weight of the dialysate solution, about 0.70% by weight to about 24% by weight of the dialysate solution, about 0.72% by weight to about 24% by weight of the dialysate solution, about 0.74% by weight to about 24% by weight of the dialysate solution, about 0.76% by weight to about 24% by weight of the dialysate solution, about 0.78% by weight to about 24% by weight of the dialysate solution, about 0.80% by weight to about 24% by weight of the dialysate solution, about 0.82% by weight to about 24% by weight of the dialysate solution, about 0.84% by weight to about 24% by weight of the dialysate solution, about 0.86% by weight to about 24% by weight of the dialysate solution, about 0.88% by weight to about 24% by weight of the dialysate solution, about 0.90% by weight to about 24% by weight of the dialysate solution, about 0.92% by weight to about 23% by weight of the dialysate solution, about 0.94% by weight to about 23% by weight of the dialysate solution, about 0.96% by weight to about 23% by weight of the dialysate solution, about 0.98% by weight to about 23% by weight of the dialysate solution, about 1.00% by weight to about 23% by weight of the dialysate solution, about 1.02% by weight to about 22% by weight of the dialysate solution, about 1.04% by weight to about 22% by weight of the dialysate solution, about 1.06% by weight to about 22% by weight of the dialysate solution, about 1.08% by weight to about 22% by weight of the dialysate solution, about 1.10% by weight to about 22% by weight of the dialysate solution, about 1.12% by weight to about 21% by weight of the dialysate solution, about 1.14% by weight to about 21% by weight of the dialysate solution, about 1.16% by weight to about 21% by weight of the dialysate solution, about 1.18% by weight to about 21% by weight of the dialysate solution, about 1.20% by weight to about 21% by weight of the dialysate solution, about 1.21% by weight to about 20% by weight of the dialysate solution, about 1.22% by weight to about 20% by weight of the dialysate solution, about 1.23% by weight to about 20% by weight of the dialysate solution, about 1.24% by weight to about 20% by weight of the dialysate solution, or about 1.25% by weight to about 20% by weight of the dialysate solution.

In a further embodiment, the dialysate has an osmolarity between about 150 milliosmols per liter and about 1500 milliosmols per liter, about 150 milliosmols per liter and about 1480 milliosmols per liter, about 150 milliosmols per liter and about 1460 milliosmols per liter, about 150 milliosmols per liter and about 1440 milliosmols per liter, about 160 milliosmols per liter and about 1420 milliosmols per liter, about 160 milliosmols per liter and about 1400 milliosmols per liter, about 160 milliosmols per liter and about 1380 milliosmols per liter, about 160 milliosmols per liter and about 1360 milliosmols per liter, about 170 milliosmols per liter and about 1340 milliosmols per liter, about 170 milliosmols per liter and about 1320 milliosmols per liter, about 170 milliosmols per liter and about 1300 milliosmols per liter, about 170 milliosmols per liter and about 1280 milliosmols per liter, about 180 milliosmols per liter and about 1260 milliosmols per liter, about 180 milliosmols per liter and about 1240 milliosmols per liter, about 180 milliosmols per liter and about 1220 milliosmols per liter, about 180 milliosmols per liter and about 1200 milliosmols per liter, about 200 milliosmols per liter and about 1180 milliosmols per liter, about 200 milliosmols per liter and about 1160 milliosmols per liter, about 200 milliosmols per liter and about 1140 milliosmols per liter, about 200 milliosmols per liter and about 1120 milliosmols per liter, about 210 milliosmols per liter and about 1100 milliosmols per liter, about 210 milliosmols per liter and about 1080 milliosmols per liter, about 210 milliosmols per liter and about 1060 milliosmols per liter, about 210 milliosmols per liter and about 1040 milliosmols per liter, about 220 milliosmols per liter and about 1020 milliosmols per liter, about 220 milliosmols per liter and about 1000 milliosmols per liter, about 220 milliosmols per liter and about 980 milliosmols per liter, about 220 milliosmols per liter and about 960 milliosmols per liter, about 230 milliosmols per liter and about 940 milliosmols per liter, about 230 milliosmols per liter and about 920 milliosmols per liter, about 230 milliosmols per liter and about 900 milliosmols per liter, about 230 milliosmols per liter and about 880 milliosmols per liter, about 240 milliosmols per liter and about 860 milliosmols per liter, about 240 milliosmols per liter and about 840 milliosmols per liter, about 240 milliosmols per liter and about 820 milliosmols per liter, about 240 milliosmols per liter and about 800 milliosmols per liter, about 260 milliosmols per liter and about 780 milliosmols per liter, about 260 milliosmols per liter and about 760 milliosmols per liter, about 260 milliosmols per liter and about 740 milliosmols per liter, about 260 milliosmols per liter and about 720 milliosmols per liter, about 280 milliosmols per liter and about 700 milliosmols per liter, about 280 milliosmols per liter and about 680 milliosmols per liter, about 280 milliosmols per liter and about 660 milliosmols per liter, about 280 milliosmols per liter and about 640 milliosmols per liter, about 290 milliosmols per liter and about 620 milliosmols per liter, about 290 milliosmols per liter and about 600 milliosmols per liter, about 290 milliosmols per liter and about 580 milliosmols per liter, about 290 milliosmols per liter and about 560 milliosmols per liter, about 290 milliosmols per liter and about 540 milliosmols per liter, about 290 milliosmols per liter and about 520 milliosmols per liter, about 290 milliosmols per liter and about 500 milliosmols per liter, about 290 milliosmols per liter and about 480 milliosmols per liter, about 290 milliosmols per liter and about 460 milliosmols per liter, or about 290 milliosmols per liter and about 450 milliosmols per liter, In another embodiment, the polyglycerol has a polydispersity of about 1.0 to 15, about 1.0 to about 14, about 1.0 to about 13, about 1.0 to about 12, about 1.0 to about 11, about 1.0 to about 10, about 1.0 to about 9, about 1.0 to about 8, about 1.0 to about 7, about 1.0 to about 6 or about 1.0 to about 5.

In one embodiment, the degree of branching of the polyglycerol is between about 0.5 and about 0.7, about 0.6 and about 0.7, about 0.5 and about 0.6, about 0.55 and about 0.7, or about 0.55 and about 0.65.

In another embodiment, the dialysate comprises first, second or more polyglycerols wherein the molecular weight of each of the first, second or more polyglycerols is different from the molecular weight of the other first, second or more polyglycerols.

In another embodiment, the polyglycerol may further comprise one or more hydrophobic groups, hydrophilic groups or both. In one embodiment, the one or more hydrophobic groups, hydrophilic groups or both are joined to form about 1% to about 100% of the hydroxyl groups on the polyglycerol. In another embodiment, the one or more hydrophobic groups, hydrophilic groups or both are joined to form about 1% to about 40% of the hydroxyl groups on the polyglycerol. In a further embodiment, the one or more hydrophobic groups, hydrophilic groups or both comprise one or more of a carboxylic acid, an amine, a substituted amine, an amino acid, a phosphate, a sulfate, an alkyl, an alkyl ether, an aromatic group, a zwitterionic group, a carbohydrate, a disulfide or a thiol.

In one embodiment, the dialysate further comprises one or more electrolytes. In another embodiment, the dialysate further comprises one or more amino acids. In a further embodiment, the dialysate further comprises one or more diffusion agents. In another embodiment, the dialysate further comprises one or more osmotic agents. In one embodiment, the osmotic agent or diffusion agent comprises sodium, chloride, lactate, bicarbonate, a bicarbonate producing agent, calcium, potassium, magnesium, dextrose, fructose, glycerol, sorbitol, manitol, L-carnitine, bovine serum albumin (BSA), maltose, maltotriose, maltopentose or xylitol.

In another aspect, use of a dialysate as described herein for transport of molecules, solutes or ions across a membrane, a semi-permeable membrane, a biomembrane, a synthetic semi-permeable membrane or a combination thereof is disclosed.

In another aspect, use of a dialysate as described herein in dialysis is disclosed. In one embodiment, the dialysis comprises intermittent dialysis. In another embodiment, the dialysis comprises continuous dialysis. In another embodiment, the dialysate is separated by a semi-permeable membrane from a bodily fluid wherein water, toxins, molecules, ions or waste products flow from the bodily fluid through the semi-permeable membrane and into the dialysate. In a further embodiment, the dialysate is used in parallel with a filter to sterilize a dialysis solution or to remove toxins, molecules, ions or waste products therefrom.

In another aspect, use of a dialysate as described herein in peritoneal dialysis is disclosed. In one embodiment, the peritoneal dialysis comprises continuous ambulatory peritoneal dialysis. In another embodiment, the peritoneal dialysis comprises cycler peritoneal dialysis. In another embodiment, the dialysate as described herein is used in combination with at least one other peritoneal dialysis solution. In a further embodiment, the dialysate is used in conjunction with electrolyte administration.

In a further aspect, use of a dialysate as described herein in hemodialysis is disclosed. In one embodiment, the dialysate is used in combination with at least one other hemodialysis solution.

In one aspect, use of a dialysate as described herein in renal replacement therapy is disclosed.

In another aspect, the present invention provides a dialysis solution comprising a dialysate as described herein.

In a further aspect, the present invention provides a peritoneal dialysis solution comprising a dialysate as described herein.

In accordance with a further aspect of the invention, methods are provided for treating a patient having end-stage renal disease, the methods comprising administering a dialysate as described herein to the patient during peritoneal dialysis. In one embodiment, the dialysate may be administered more than once per day.

In another aspect, use of a dialysate as described herein as an intravascular volume expander or as an intravenous diuretic is disclosed.

In another aspect, use of a dialysate as described herein to treat a patient having edema, increased intracranial pressure, poisoning or an electrolyte disturbance is disclosed. In one embodiment, the edema comprises cerebral edema.

In one aspect, the present invention provides a kit for formulating a dialysis solution, the kit comprising a lyophilized polyglycerol wherein the polyglycerol is of a molecular weight between about 0.15 kDa and about 60 kDa and instructions for using the lyophilized polyglycerol for formulating the dialysis solution. In one embodiment, the molecular weight of the polyglycerol is between about 0.16 kDa and about 59 kDa, about 0.17 kDa and about 58 kDa, about 0.18 kDa and about 57 kDa, about 0.19 kDa and about 56 kDa, about 0.20 kDa and about 55 kDa, about 0.21 kDa and about 54 kDa, about 0.22 kDa and about 53 kDa, about 0.23 kDa and about 52 kDa, about 0.24 kDa and about 51 kDa, about 0.25 kDa and about 50 kDa, about 0.26 kDa and about 49 kDa, about 0.27 kDa and about 48 kDa, about 0.28 kDa and about 47 kDa, about 0.29 kDa and about 46 kDa, about 0.30 kDa and about 45 kDa, about 0.31 kDa and about 44 kDa, about 0.32 kDa and about 43 kDa, about 0.33 kDa and about 42 kDa, about 0.34 kDa and about 41 kDa, about 0.35 kDa and about 40 kDa, about 0.36 kDa and about 39 kDa, about 0.37 kDa and about 38 kDa, about 0.38 kDa and about 37 kDa, about 0.39 kDa and about 36 kDa, about 0.40 kDa and about 35 kDa, about 0.41 kDa and about 34 kDa, about 0.42 kDa and about 33 kDa, about 0.43 kDa and about 32 kDa, about 0.44 kDa and about 31 kDa, about 0.45 kDa and about 30 kDa, about 0.46 kDa and about 29 kDa, about 0.47 kDa and about 28 kDa, about 0.48 kDa and about 27 kDa, about 0.49 kDa and about 26 kDa, about 0.50 kDa and about 25 kDa, about 0.50 kDa and about 24 kDa, about 0.50 kDa and about 23 kDa, about 0.50 kDa and about 22 kDa, about 0.50 kDa and about 21 kDa, about 0.50 kDa and about 20 kDa, about 0.50 kDa and about 19 kDa, about 0.50 kDa and about 18 kDa, about 0.50 kDa and about 17 kDa, about 0.50 kDa and about 16 kDa, about 0.50 kDa and about 15 kDa, about 0.50 kDa and about 14 kDa, about 0.50 kDa and about 13 kDa, about 0.50 kDa and about 12 kDa, about 0.50 kDa and about 11 kDa, about 0.50 kDa and about 10 kDa, about 0.50 kDa and about 9 kDa, about 0.50 kDa and about 8 kDa, about 0.50 kDa and about 7 kDa, about 0.50 kDa and about 6 kDa, about 0.50 kDa and about 5 kDa, about 0.50 kDa and about 4 kDa, or about 0.50 kDa and about 3 kDa. In another embodiment, the kit further comprises one or more electrolytes. In another embodiment, the kit further comprises one or more amino acids. In a further embodiment, the kit further comprises one or more diffusion agents. In another embodiment, the kit further comprises one or more osmotic agents. In one embodiment, the osmotic agent or diffusion agent comprises sodium, chloride, lactate, bicarbonate, a bicarbonate producing agent, calcium, potassium, magnesium, dextrose, fructose, glycerol, sorbitol, manitol, L-carnitine, bovine serum albumin (BSA), maltose, maltotriose, maltopentose or xylitol.

In another aspect, the present invention provides a kit for formulating a dialysis solution, the kit comprising a dialysate as described herein and instructions for formulating the dialysis solution.

In a further aspect, the present invention provides a composition comprising a dialysate as described herein and at least one physiologically acceptable salt, buffer, diluent or excipient, for use as a dialysis solution. In one embodiment, the composition is in aqueous solution. In another embodiment, the composition is a lyophilized product.

In another aspect, the present invention provides a peritoneal dialysis solution comprising a hyperbranched polyglycerol wherein the hyperbranched polyglycerol is of a molecular weight between about 0.15 kDa and about 60 kDa. In one embodiment, the molecular weight of the polyglycerol is between about 0.16 kDa and about 59 kDa, about 0.17 kDa and about 58 kDa, about 0.18 kDa and about 57 kDa, about 0.19 kDa and about 56 kDa, about 0.20 kDa and about 55 kDa, about 0.21 kDa and about 54 kDa, about 0.22 kDa and about 53 kDa, about 0.23 kDa and about 52 kDa, about 0.24 kDa and about 51 kDa, about 0.25 kDa and about 50 kDa, about 0.26 kDa and about 49 kDa, about 0.27 kDa and about 48 kDa, about 0.28 kDa and about 47 kDa, about 0.29 kDa and about 46 kDa, about 0.30 kDa and about 45 kDa, about 0.31 kDa and about 44 kDa, about 0.32 kDa and about 43 kDa, about 0.33 kDa and about 42 kDa, about 0.34 kDa and about 41 kDa, about 0.35 kDa and about 40 kDa, about 0.36 kDa and about 39 kDa, about 0.37 kDa and about 38 kDa, about 0.38 kDa and about 37 kDa, about 0.39 kDa and about 36 kDa, about 0.40 kDa and about 35 kDa, about 0.41 kDa and about 34 kDa, about 0.42 kDa and about 33 kDa, about 0.43 kDa and about 32 kDa, about 0.44 kDa and about 31 kDa, about 0.45 kDa and about 30 kDa, about 0.46 kDa and about 29 kDa, about 0.47 kDa and about 28 kDa, about 0.48 kDa and about 27 kDa, about 0.49 kDa and about 26 kDa, about 0.50 kDa and about 25 kDa, about 0.50 kDa and about 24 kDa, about 0.50 kDa and about 23 kDa, about 0.50 kDa and about 22 kDa, about 0.50 kDa and about 21 kDa, about 0.50 kDa and about 20 kDa, about 0.50 kDa and about 19 kDa, about 0.50 kDa and about 18 kDa, about 0.50 kDa and about 17 kDa, about 0.50 kDa and about 16 kDa, about 0.50 kDa and about 15 kDa, about 0.50 kDa and about 14 kDa, about 0.50 kDa and about 13 kDa, about 0.50 kDa and about 12 kDa, about 0.50 kDa and about 11 kDa, about 0.50 kDa and about 10 kDa, about 0.50 kDa and about 9 kDa, about 0.50 kDa and about 8 kDa, about 0.50 kDa and about 7 kDa, about 0.50 kDa and about 6 kDa, about 0.50 kDa and about 5 kDa, about 0.50 kDa and about 4 kDa, or about 0.50 kDa and about 3 kDa. In another embodiment, the peritoneal dialysis solution further comprises one or more electrolytes. In another embodiment, the peritoneal dialysis solution further comprises one or more amino acids. In a further embodiment, the peritoneal dialysis solution further comprises one or more diffusion agents. In another embodiment, the peritoneal dialysis solution further comprises one or more osmotic agents. In one embodiment, the osmotic agent or diffusion agent comprises sodium, chloride, lactate, bicarbonate, a bicarbonate producing agent, calcium, potassium, magnesium, dextrose, fructose, glycerol, sorbitol, manitol, L-carnitine, bovine serum albumin (BSA), maltose, maltotriose, maltopentose or xylitol.

In another aspect, a dialysate as described herein may be used in the treatment of renal failure, kidney disease, poisoning, edema or an electrolyte disturbance.

In accordance with another aspect of the invention, methods are provided for treating renal failure, kidney disease, poisoning, edema or an electrolyte disturbance in a patient, the methods comprising administering a dialysate as described herein to the patient.

In accordance with a further aspect of the invention, ex vivo methods are provided for removing toxins, molecules, ions or waste products from a bodily fluid, the method comprising separating a dialysate as described herein from the bodily fluid by a semi-permeable membrane and allowing the toxins, molecules, ions or waste products to flow from the bodily fluid through the semi-permeable membrane and into the dialysate.

In another aspect, use of a dialysate as described herein in dialysis in a mammal is disclosed.

DETAILED DESCRIPTION

Figure 1A:
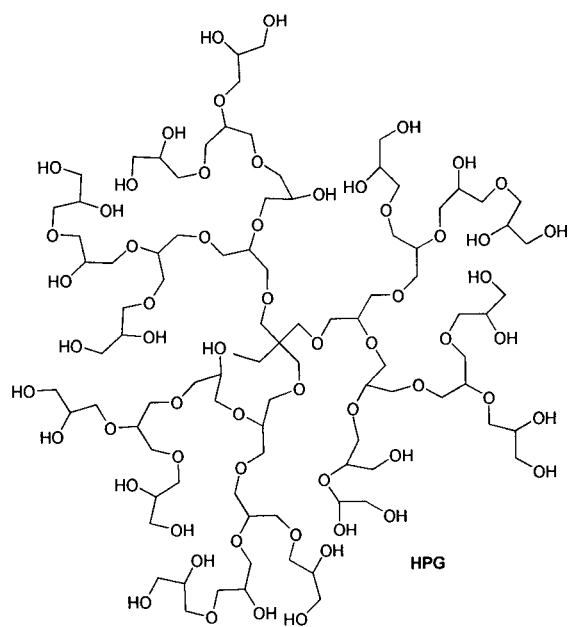
FIGS. 1A and 1B show chemical structures of a hyperbranched polyglycerol (HPG) and a linear polyglycerol (LPG) respectively, and "n" in FIG. 1B may range from about 1 to about 810.

Any terms not directly defined herein shall be understood to have the meanings commonly associated with them as understood within the art of the invention.

The term "polyglycerol" is used herein as it is normally understood to a person of ordinary skill in the art and often refers to a polymer having a degree of branching, e.g., between 0 and 1.0 wherein the number of hydroxyl groups is equal to the number of repeat units and the repeat units consist of the following (wherein "r" is the repeat unit):

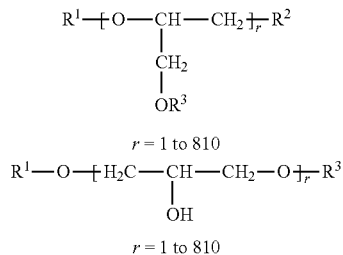

wherein $R^1$ is H—, $CH_3$—, $CH_3CH_2$—, t-Bu-, $N_3$—$CH2$-$CH_2$, alkyl chains (1 to 18 carbons), —$CH_2$—$NH_2$, —$CH_2$—$N(CH_3)_2$, —$CH_2$—$NH(CH_3)$, r-, r-$CH_2$— or (r-)$_2$CH—; $R^2$ is -r, —O-r, —O—$CH_2$—CH-r, or —OH; and $R^3$ is —H, —$CH_3$, —$CH_2$—$CH_3$, r-, —$CH_2$-r or —CH(-r)$_2$. The foregoing repeat units are not limited to the stereochemistry shown. Examples of "polyglycerol" include a hyperbranched polyglycerol (HPG), a linear polyglycerol (LPG), or dendritic polyglycerol/polyglycerol dendrimer or chemically modified polyglycerol or biodegradable polyglycerol, comb-like polyglycerol or dendri-graft polyglycerol or cyclic polyglycerol or a combination thereof. The embodiments of the polyglycerol as described herein include all possible stereochemical alternatives, including those illustrated or described herein.

The term "hyperbranched polyglycerol" is used herein as it is normally understood to a person of ordinary skill in the art and often refers to a polyglycerol having a degree of branching between about 0.4 and about 0.7.

The term "linear polyglycerol" is used herein as it is normally understood by a person of ordinary skill in the art, and often refers to a polyglycerol having degree of branching "zero".

The term "dendritic polyglycerol or polyglycerol dendrimer" is used herein as it is normally understood by a person of ordinary skill in the art, and often refers to a polyglycerol having degree of branching 1.0.

The term "dialysate" is used herein as it is normally understood to a person of ordinary skill in the art and often refers to a substance that can act as one or both of a diffusion agent and an osmotic agent.

The term "osmotic agent" is used herein as it is normally understood to a person of ordinary skill in the art and often refers to a substance that creates an osmotic gradient across a semi-permeable membrane to cause the movement of water across the membrane.

The term "diffusion agent" is used herein as it is normally understood to a person of ordinary skill in the art and often refers to a substance that creates a concentration gradient across a membrane to cause the movement of solutes from an area of higher solute concentration to an area of lower solute concentration.

The term "electrolyte" is used herein as it is normally understood to a person of ordinary skill in the art and often refers to an ionized solute.

The dialysates described herein comprise a polyglycerol. In various embodiments, the polyglycerol may be of a molecular weight between about 0.15 kDa and about 60 kDa or between about 0.45 kDa and about 3.0 kDa. Polyglycerol is a flexible, hydrophilic aliphatic polyether polymer which can be synthesized in linear, hyperbranched and dendrimeric forms with precise control of molecular weight. Polyglycerol and its derivatives have an excellent biocompatibility profile and multi-functionality. For example, it is highly blood compatible, non-immunogenic and non-toxic with no evidence of animal toxicity (Kainthan, R. K., et al., (2006) *Biomaterials* 27(31): 5377-5390; Kainthan, R. K., et al., (2008) *Biomaterials* 29(11): 1693-1704). The circulation half-life in mice depends on the molecular weight of the polymer, but may reach about 60 hours for a molecular weight of 540 kDa and can be finely tuned. Unlike other polymers, polyglycerol has shown very limited organ accumulation after intravenous injection (Kainthan, R. K., et al., (2007) *Biomaterials* 28(31): 4581-4590; Kainthan, R. K., et al., (2008) *Biomaterials* 29(11): 1693-1704). Furthermore, this inert polymer contains no glucose or carbohydrate, it is stable and easily delivered at physiological pH.

Figure 1B:
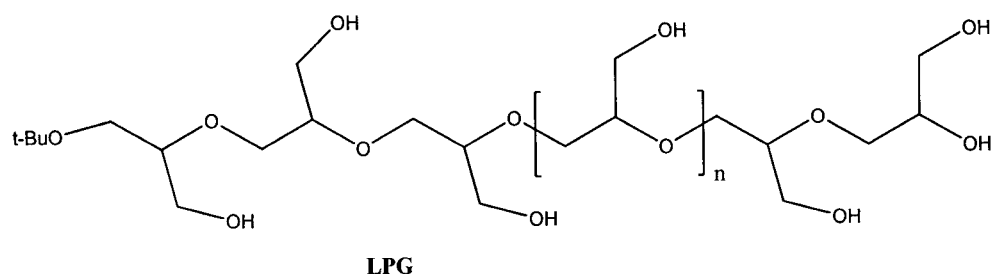

Hyperbranched polyglycerol (HPG), which is, for example, a polyglycerol having a degree of branching between about 0.4 and about 0.7, may be prepared, for example, by multi-branching ring opening polymerization of glycidol under slow monomer addition. Polyglycerol dendrimers are prepared by multiple organic reactions. A representative structure of an embodiment of HPG is shown in FIG. 1A. The structure contains large and small branches with hydroxyl-functionalities that render HPG a highly functional material. Linear polyglycerol (LPG) may be prepared, for example, by ring opening polymerization of ethoxy ethyl glycidyl ether using t-BuO⁻K⁺ as initiator in the presence of 1,4-dioxane followed by deprotection in HCl (Gervais, M., et al., (2010) *Macromolecules* 43: 1778-1784; Stiriba, S., et al., (2002) *J. Am. Chem. Soc.* 124: 9698-9700;

Kainthan, R. K., et al., *Biomacromolecules* 7: 703-709). A representative structure of an embodiment of LPG is shown in FIG. 1B.

Polyglycerol has been investigated for its potential in many biomedical applications. Moreover, polyglycerol is even less cytotoxic and thermally and oxidatively more stable than poly(ethylene glycol) (PEG).

Polyglycerol is a clear, viscous liquid. At room temperature, it is highly viscous and essentially non-volatile. Both linear and hyperbranched polyglycerols are of a compact nature in solution and highly soluble in water (for example, HPG has a water solubility greater than 200 mg/mL). The hydrodynamic radius ($R_h$) of a LPG with $M_n$=104,000 in aqueous 0.1 N $NaNO_3$ solution may be 4.55 nm as determined by QELS measurements. For comparison, the $R_h$ value of an HPG with $M_n$=104,000 may be 4.85 nm and a PEG with similar molecular weight may be 12.23 nm. The very small $R_h$ value of LPG indicates that it has quite a different solution structure compared to other linear water soluble polymers and more closely approximates the solution structure and properties of HPG. In terms of intrinsic viscosity, LPG has an intrinsic viscosity (0.047 dL/g) that is more similar to that of HPG (0.052 dL/g) than PEG (1.308 dL/g), which again suggests that LPG has a highly compact structure in solution. The intrinsic viscosity of polyglycerol increases with increasing molecular weight (similar to proteins) and is significantly lower than other linear polymers. This suggests that polyglycerol can not only be used as an osmotic agent like other macromolecules, but may also actively dissolve waste from the circulation, and therefore, act as a diffusion agent.

In various embodiments, the dialysates as described herein may have a pH between about 2.0 and about 9.0 or between about 6.5 and about 7.5.

In various embodiments, the dialysates as described herein may be in aqueous solution, wherein the polylgycerol comprises about 0.01% by weight to about 50% by weight of the dialysate solution or between about 1.25% by weight to about 20% by weight of the dialysate solution.

In various embodiments, the dialysates as described herein may have an osmolarity between about 150 milliosmols per liter and about 1500 milliosmols per liter. For peritoneal dialysis applications, the osmolarity may be between about 290 milliosmols per liter and about 450 milliosmols per liter. For ex vivo applications, high osmolarity may be used; for example, about 1500 milliosmols per liter can be achieved using about 40 wt. % to about 50 wt. % 0.5 kDa HPG solutions. With lower molecular weight HPGs, this osmolarity may be achieved with about 30 wt. % to about 40 wt. % HPG solutions In various embodiments, the dialysates as described herein may have a polydispersity between about 1.0 and 15 for polyglycerol.

In various embodiments, the dialysates as described herein may comprise first, second or more polyglycerols wherein the molecular weight of each of the first, second or more polyglycerols is different from the molecular weight of the other first, second or more polyglycerols. The molecular weights of each of the first, second or more polyglycerols may vary by as little as 74 Da, corresponding to the approximate weight of one repeat unit. The molecular weights may also vary by amounts such as about 0.5 kDa, about 1 kDa, about 2 kDa or about 2.5 kDa.

During peritoneal dialysis, the dwell time required for removing water and solutes from the blood appears to depend on the molecular weight of the polyglycerol which in turn affects the osmolality of the polyglycerol. In various embodiments, by preparing a dialysate with specific combinations of different molecular weights, the dwell time required for effective dialysis may be tailored for a specific situation. Various proportions of each polyglycerol may be used, depending again on the desired dwell time. A combination of polyglycerols may be obtained in a variety of ways, for example, by minimizing purification after synthesis so that the polyglycerol has a larger polydispersity or by combining different polyglycerols having a narrow polydispersity.

In various embodiments, the polyglycerols as described herein may be derivatized. Derivatives of polyglycerol may include polymers which contain hydrophobic groups, hydrophilic groups or both, which have been added to the polymer. Such regions may be provided by derivatizing the hydroxyl groups of the polymer. A functional derivative may be bound to about 1% to about 100% of hydroxyl groups on the polyglycerol, or to about 1% to about 40% of hydroxyl groups on the polyglycerol. By adding such groups to the polyglycerol, the number of hydroxyl groups may no longer be equal to the number of repeat units in the polyglycerol. Methodologies for adding such groups to a polyglycerol are known to a person of ordinary skill in the art (Kainthan, R. K., et al., (2008) *Biomaterials* 29: 1693-1704; Kizhakkedathu, J. N., et al., (2010) *Biomacromolecules* 11: 2567; Kainthan, R. K., et al., (2006) *Biomaterials* 27: 5377-5390; Turk, H., et al., (2004) *Bioconjugate Chem.* 15: 162; Dernedde, J., et al., (2010) *Proc. Nat. Acad. Sci.* 107: 19679; Calderon, M., et al., (2010) *Adv. Mater.* 22: 190; Wilms, D., et al., (2010) *Acc. Chem. Res.* 43: 129; Baudette, P., et al., (2011) *Anal. Chem.* 83: 6500). Examples of hydrophobic groups and hydrophilic groups include a carboxylic acid, an amine, a substituted amine, quaternary amine, an amino acid, a phosphate, a sulfate, sulfonate, phosphonate, an alkyl, alkene, alkyne, an alkyl ether, an aromatic, an aromatic ether, a zwitterionic group, a carbohydrate, a disulfide, a ketal, a substituted ketal, acetal, a substituted acetal, ester groups, thioesters, urethane, ester-amides, amide groups, a peptide, phenol, halogens or a thiol.

In various embodiments, the dialysates as described herein may further comprise one or more electrolytes, one or more amino acids, one or more diffusion agents, and/or one or more osmotic agents. The diffusion agent or osmotic agent may comprise sodium, chloride, lactate, bicarbonate, a bicarbonate producing agent, calcium, potassium, magnesium, dextrose, fructose, glycerol, sorbitol, manitol, L-carnitine, bovine serum albumin (BSA), maltose, maltotriose, maltopentose or xylitol, synthetic or natural polymers.

In various embodiments, the dialysates as described herein may act as an osmotic agent and/or diffusion agent and as a result, may be used in the transport of molecules, solutes or ions across a membrane, a semi-permeable membrane, a biomembrane, a synthetic semi-permeable membrane or a combination thereof. The dialysates as described herein may therefore be used in the treatment of any condition requiring the removal of water or solutes from a bodily fluid, a cavity or any other biological system. Examples of such treatment include the use of the dialysates as described herein as an intravascular volume expander or an intravenous diuretic. The dialysates as described herein may be used to treat a patient having kidney disease, edema (including a cerebral edema), increased intracranial pressure, poisoning or an electrolyte disturbance, or may be used in renal replacement therapy.

The dialysates as described herein may be used in dialysis. The dialysis may be either intermittent dialysis or continuous dialysis. The dialysis may be conducted for a mammal. The dialysate may be separated from a bodily fluid by a semi-permeable membrane wherein water, toxins, molecules, ions or waste products flow from the bodily fluid through the semi-permeable membrane and into the dialysate. A dialysate as described herein may be used in parallel with a filter to sterilize a dialysis solution or to remove toxins, molecules, ions or waste products therefrom.

The dialysates as described herein may be used in peritoneal dialysis, including continuous ambulatory peritoneal dialysis (CAPD) or cycler peritoneal dialysis. Alternatively, the dialysates as described herein may be used in hemodialysis. The dialysate may be used in conjunction with medication administered intraperitonealy and/or with electrolyte administration. The dialysates as described herein may be used in combination with at least one other peritoneal dialysis solution or at least one other hemodialysis solution, as applicable. A dialysis solution or peritoneal dialysis solution may comprise a dialysate as described herein. The dialysis solution or peritoneal dialysis solution may comprise a HPG as described herein.

As shown below, in a rat model of acute PD, a HPG PD solution can induce concentration/osmolality-dependent fluid removal, and shows improved properties as compared to glucose-based PD solutions in terms of urea clearance. Furthermore, there is less peritoneal membrane injury and inflammation induced by HPG as compared to a glucose-based PD solution, as shown by increased survival of human peritoneal mesothelial cells (HPMCs) in vitro following exposure to a HPG PD solution.

During PD, fluid flows through the peritoneal membrane to the PD solution due to osmotic pressure generated by an increase in the osmolality from the plasma to the PD solution. In addition to fluid or water removal, PD also requires the removal of waste products from the body (e.g. urea, glucose, creatinine, phosphate and other metabolic byproducts, all of which may be considered as any one of a toxin, molecule, ion or waste product to be removed during dialysis). This removal is driven by diffusion via the concentration gradients between the plasma and PD solution. A PD solution comprising a polyglycerol as described herein may perform both of these functions.

The greater biocompatibility of PD solutions comprising a polyglycerol as described herein as compared to conventional glucose-based PD solutions in the acute model of PD described below, provides evidence of enhanced tolerance by the peritoneum. Hyperosmotic glucose-based PD solutions induce cellular injury to all types of peritoneal cells, including polymorphonuclear cells, phagocytes (i.e. macrophages) and mesothelial cells (MCs). This injury may be associated with the acidic nature and high concentration of glucose typically used. In both the in vivo model and cultured HPMCs, HPG PD solutions exhibited less injury to the peritoneum and cell cultures than a conventional PD solution under the same or higher osmolality, indicated by less peritoneum membrane injury, less leukocyte infiltration and more cell survival. Furthermore, in cultured HPMCs, most of the cells die by necrosis after exposure to PDS, which is different from the apoptosis induced by HPG PD solutions. These different mechanisms of cell death trigger different immune responses. Apoptotic cells induce immune tolerance while necrotic cells stimulate cytotoxic immunity and uptake of apoptotic cells by macrophages that promote cell growth and wound healing through the release of vascular endothelial growth factor and transforming growth factor-β. Without being bound by any particular theory, it is expected that the apoptotic cells induced by hyperosmotic HPG PD solutions during PD may not cause secondary peritoneal injury due to its induction of immune tolerance and may also be beneficial to injury repair after PD.

In various embodiments, the dialysates as described herein may be included in a kit for formulating a dialysis solution. The kit may comprise a lyophilized polyglycerol as described herein and instructions for using the lyophilized polyglycerol for formulating the dialysis solution. The kit may comprise other components of the dialysis solution, including electrolytes, amino acids, one or more other diffusion agents and/or one or more other osmotic agents. A kit for formulating a dialysis solution may also comprise a dialysate as described herein and instructions for using the dialysate for formulating the dialysis solution.

In various embodiments, the dialysates as described herein may be included in a composition. The composition may comprise a dialysate as described herein and at least one physiologically acceptable salt, buffer, diluent or excipient, for use as a dialysis solution or a peritoneal dialysis solution. The composition may be in aqueous solution or a lyophilized product.

The dialysates as described herein may be administered to a patient having end-stage renal disease during peritoneal dialysis. The dialysate may be administered more than once per day.

The dialysates as described herein may also be administered to a patient having renal failure, kidney disease, poisoning, edema or an electrolyte disturbance.

The dialysates as described herein may be used for removing toxins, molecules, ions or waste products from a bodily fluid ex vivo. The dialysate as described herein is separated from the bodily fluid by a semi-permeable membrane and the toxins, molecules, ions or waste products flow from the bodily fluid through the semi-permeable membrane and into the dialysate.

Various alternative embodiments and examples are described herein. These embodiments and examples are illustrative and should not be construed as limiting the scope of the invention.

EXAMPLES

For all examples, male inbred Spragle-Dawley rats (~300 g body weight, 10-12 weeks old) were purchased from the Charles River Laboratories International, Inc. (Wilmington, Mass., USA) and maintained in the animal facility of the Jack Bell Research Centre of the University of British Columbia (Vancouver, British Columbia, Canada). Animal experiments were performed in accordance with the Canadian Council on Animal Care guidelines under protocols approved by the Animal Use Subcommittee at the University of British Columbia.

All data are presented as mean±standard deviation (SD) of each group. Student's t-test with two-tailed distribution or ANOVA was used as appropriate for data analyses. A p value of ≤0.05 was considered significant.

Human peritoneal mesothelial cells (HPMCs) were isolated from peritoneal dialysis (PD) effluents, donated by anonymous PD patients in our clinic, following the protocol approved by the Clinical Research Ethics Board at the University of British Columbia. HPMCs were immortalized with origin deficient SV40 DNA. Both primary and SV40-immortalized HPMCs were grown in complete K1 medium as known to a person of ordinary skill in the art.

Example 1: Effect of HPG Concentration on Dialysis Efficacy in Preclinical Models One function of PD in treating patients is to remove the body's fluid, also known as ultrafiltration. The fluid removal of a HPG PD solution at varying concentrations or osmolalities was determined in rats after 4 h of acute PD and compared to a basal control at 0 h.

After initial screening of the different sizes of HPG, 3 kDa HPG was chosen for further testing in the animal model. PD solutions using HPG (MW 3 kDa, polydispersity estimated at about 1.1) at various concentrations from 2.5 to 15 wt. % were prepared. HPG was synthesized according to methods known to a person of ordinary skill in the art. After synthesis, the polymer was dialyzed in water for two days, and recovered by freeze-drying. The synthesis of HPG was verified by gel permeation chromatography and proton nuclear magnetic resonance spectroscopy. HPG PD solutions (2.5% to 15%) were prepared by dissolving HPG (2.5 g to 15 g) in 100 mL of a sterile electrolyte solution containing sodium chloride (NaCl, 53.8 mg/L), sodium lactate ($NaC_3H_5O_3$, 44.8 mg/L), calcium chloride ($CaCl_2.2H_2O$, 1.83 mg/L) and potassium chloride ($MgCl_2.6H_2O$, 0.508 mg/L). The chemical profile of the solutions was comparable to conventional PD solutions, without glucose or dextrose, and had the following ionic concentrations: 131 meq/L Na, 97 meq/L Cl, 39.9 meq/L lactate, 2.3 meq/L Ca and 0.5 meq/L Mg. The osmolality of each solution was measured using Advanced® Model 3320 Micro-Osmometer (Advanced Instruments Inc., Norwood, Mass., USA) in the Chemistry Laboratory at the Vancouver Coastal Health Regional Laboratory Medicine (Vancouver, BC, Canada) and the pH of each HPG solution was recorded using a laboratory pH meter (Accumet® B15 Basic, Fisher Scientific, Toronto, Ontario, Canada) in a period of 10 minutes. The osmolality, density and pH of each solution is shown in Table 1. The HPG solutions were compared to a conventional PD solution (Dianeal™ PD4 CAPD Solution, 2.5% dextrose, Baxter Co., Canada) (PDS).

Table 1 shows representative data relating to osmolality, density and pH of HPG (3 kDa) solutions.

TABLE 1

| Concentration of HPG (%, weight/volume) | Osmolality (mOsm/kg) | Density (g/mL) | pH* |
|---|---|---|---|
| 2.5 | 279 | 1.0240 | 6.62 (6.60-6.67) |
| 5 | 294 | 1.0264 | 6.79 (6.63-6.90) |
| 7.5 | 324 | 1.0290 | 7.19 (7.04-7.30) |
| 15 | 424 | 1.0482 | 7.22 (7.19-7.32) |

*pH values are presented as a median number.

Rats were anesthetized with isoflurane, and 30 mL of a pre-warmed HPG solution or PDS was slowly injected into the peritoneal cavity. Animals awoke within 1 to 2 minutes after the procedure and had free access to food and tap water. Either immediately or after 4 h following intraperitoneal injection, animals were euthanized with $CO_2$. Both serum and peritoneal effluent were collected from each rat, and the perital peritoneum was harvested from three rats randomly selected from each group. At 0 h, each type of HPG solution or PDS was tested in two rats, and because of no significant difference in the recovered volume from any of the groups was observed, the data accumulated from all of the solution groups (28.17±1.03 mL) was used as a basal control. The volume of peritoneal effluent was measured from each rat as a marker of ultrafiltration capacity.

Figure 2:
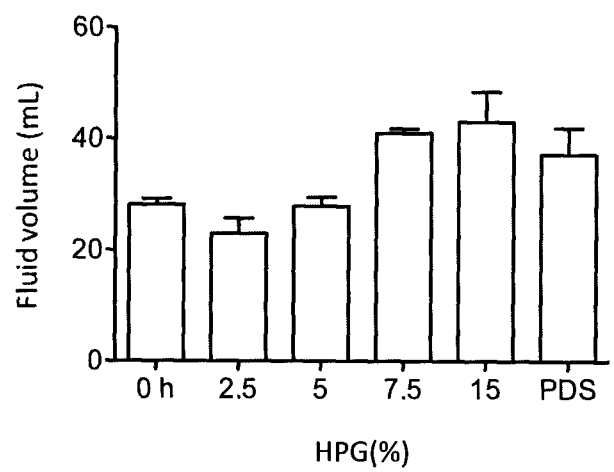
FIG. 2 shows fluid removal (ultrafiltration) induced by various HPG peritoneal dialysis (PD) solutions versus a conventional PD solution (PDS)

As shown in FIG. 2, there was a significant fluid removal induced by HPG PD solutions, indicated by a concentration-dependent increase in the volume of recovered peritoneal effluent, 40±1.24 mL by 7.5% HPG (p<0.0001, vs. basal control) and 43.33±5.24 mL by 15% HPG (p<0.0001, vs. basal control). Peritoneal effluent volume by 5% HPG solution (27.88±1.65 mL) after 4 h of dialysis was not statistically different from the basal control (p=0.7371). HPG (2.5%) did not achieve ultrafiltration at all (23.0±2.72 mL). As compared to 37.23±4.72 mL of peritoneal effluent by PDS after 4 h of dialysis (FIG. 2), the fluid removal of an HPG PD solution was the same at the concentration of 7.5% (p=0.1879), but was significantly improved at 15% (p=0.0268). These data suggests that HPG could be used as an effective osmotic agent for PD solutions and other applications.

The other function of PD is waste removal or solute clearance. Since the creatinine in peritoneal effluents in this model was below the minimal level for its measurement in the laboratory (data not shown), urea nitrogen was used as a marker of waste substances in the effluent or bloodstream. Urea levels in both the peritoneal effluents and sera were measured in the Chemistry Laboratory at the Vancouver Coastal Health Regional Laboratory Medicine using the Dimension Vista® System with BUN Flex® reagent cartridge (Siemens Healthcare Diagnostics Inc., Newark, Del., USA). The urea removal induced by HPG PD solutions versus PDS was calculated by net removal as well as clearance rate. Absolute urea removal was calculated by multiplying the urea concentration in the recovered dialysate (D) or effluent with its volume (V), and the dialysate to plasma (P) urea ratio (D/P) was calculated to assess the equilibration of urea across the peritoneal membrane. Urea clearance was calculated by multiplying the D/P ratio with the volume of the dialysate (D/P×V).

Table 2 shows representative data relating to the efficacy of waste removal by HPG (3 kDa) solutions.

TABLE 2

| Experimental Groups and Comparisons | Urea Concentration (mmol/L) | Total Urea (mmol) | Urea Clearance (mL per 4 h) |
|---|---|---|---|
| 2.5% HPG | 4.388 ± 0.383 | 0.101 ± 0.015 | 22.44 ± 3.75 |
| 5% HPG | 5.575 ± 0.427 | 0.156 ± 0.020 | 23.13 ± 3.71 |
| 7.5% HPG** | 7.30 ± 1.08 | 0.300 ± 0.047 | 36.08 ± 2.05 |
| 15% HPG* | 7.85 ± 0.74 | 0.337 ± 0.042 | 39.17 ± 5.21 |
| PDS | 5.356 ± 0.993 | 0.198 ± 0.043 | 32.01 ± 2.67 |
| p values (versus PDS) | * p = 0.0002 ** p = 0.0088 | * p < 0.0001 ** p = 0.0027 | * p = 0.0037 ** p = 0.0209 |

As indicated by Table 2, at both concentrations of 7.5% and 15% HPG, either the net urea removal or the urea clearance rate induced by the HPG PD solution was significantly higher than that of glucose-based PDS. More interestingly, the ultrafiltration induced by a 7.5% HPG PD solution was not different from that of PDS (FIG. 2), but its urea removal was more effective than that of PDS as indicated by 0.300±0.047 mmol of total urea in the peritoneal effluent of 7.5% HPG solution compared to 0.198±0.043 mmol of PDS (>51% increase, p=0.0027). This data suggest that HPG is superior to glucose in the removal of urea and perhaps other waste substances.

The same experiments relating to fluid and waste removal induced by HPG PD solutions described above were carried out for 1 kDa HPG PD solution and 0.5 kDa HPG PD solution, the results of which are shown is Tables 3 and 4.

Table 3 shows representative data relating to the efficacy of HPG (1 kDa) PD solution in acute PD.

TABLE 3

| Group | Ultrafiltration (mL) | Total Urea Removal (mmol) |
|---|---|---|
| PDS | 37.23 ± 4.72 | 0.198 ± 0.043 |
| 7.5% HPG (1 kDa) | 44.67 ± 0.58 | 0.268 ± 0.071 |
| 5% HPG (1 kDa) | 39.38 ± 1.25 | 0.206 ± 0.025 |
| 2.5% HPG (1 kDa) | 30.50 ± 0.71 | 0.145 ± 0.029 |
| p value | p = 0.0214 (7.5% HPG vs. PDS) p = 0.3956 (5% HPG vs. PDS) | p = 0.0592 (7.5% HPG vs. PDS) p = 0.7339 (5% HPG vs. PDS) |

Table 4 shows representative data relating to the efficacy of HPG (0.5 kDa) solution in acute PD.

TABLE 4

| Group | Ultrafiltration (mL) | Total Urea Removal (mmol) |
|---|---|---|
| PDS | 37.23 ± 4.72 | 0.198 ± 0.043 |
| 7.5% HPG (0.5 kDa) | 47.50 ± 3.54 | 0.245 ± 0.035 |
| 5% HPG (0.5 kDa) | 45.50 ± 3.97 | 0.231 ± 0.052 |
| 2.5% HPG (0.5 kDa) | 34.83 ± 1.26 | 0.208 ± 0.047 |
| 1.25% HPG (0.5 kDa) | 27.33 ± 1.53 | 0.163 ± 0.017 |
| p value | p = 0.0148 (7.5% HPG vs. PDS) p = 0.0174 (5% HPG vs. PDS) p = 0.414 (2.5% HPG vs. PDS) | p = 0.1844 (7.5% HPG vs. PDS) p = 0.2949 (5% HPG vs. PDS) p = 0.745 (2.5% HPG vs. PDS) |

These results indicate that smaller HPG polymers may provide improved ultrafiltration and waste removal properties as compared to larger polymers. As compared to a conventional 2.5% glucose PD solution, the same ultrafiltration can be achieved with a 7.5% HPG (3 kDa) PD solution, a 5% HPG (1 kDa) PD solution or a 2.5-5% HPG (0.5 kDa) PD solution, suggesting that less of a smaller HPG can be used to achieve equivalent results to those achieved with a conventional PD solution.

Example 2: Effect of HPG PD Solution on Peritoneal Membrane Injury and Neutrophil Infiltration Poor ultrafiltration or solute clearance largely limits PD as a long-term therapy because chronic exposure to current PD solutions causes inflammation and injury of the peritoneal membrane, which progressively undergoes fibrosis and angiogenesis, termed as encapsulating peritoneal sclerosis, eventually resulting in UFF. To demonstrate the difference of peritoneal membrane injury and inflammation in the rats receiving HPG PD solutions versus PDS, the structure and leukocyte infiltration of peritoneal membranes were examined by histological analysis, and cell population in the peritoneal effluents was analyzed with flow cytometric analysis.

Figure 3:
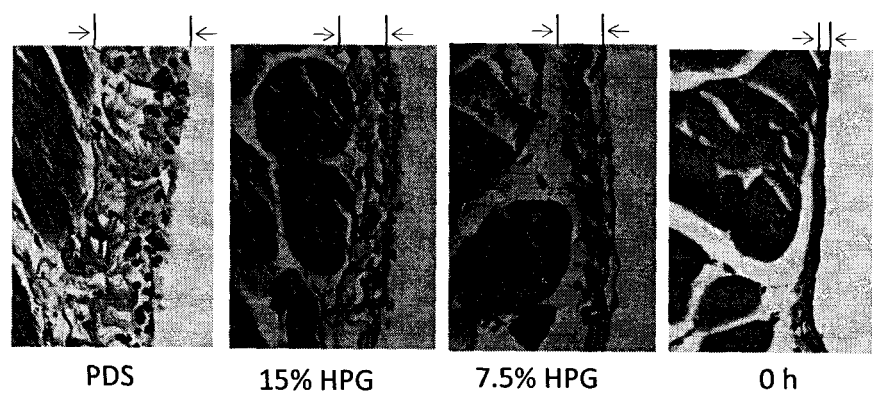
FIG. 3 shows peritoneal membrane damage and leukocyte infiltration induced by various HPG PD solutions versus PDS.

Three strips of parietal peritoneum randomly selected from each group of rats (one strip per rat) were fixed in 10% neutral buffered formalin and embedded in paraffin wax. Sections were cut at 4 μm thickness and stained with hematoxylin and eosin. The pathological parameters of peritoneal membrane injury (i.e. the increase in the thickness of the submesothelial tissue and whether the mesothelium was intact) and polymorphonuclear infiltration were examined under microscopic view (400× magnification) in two separate sections of each strip of the peritoneum in a blinded fashion. The presence of neutrophils in the recovered fluids was used as a biomarker for peritoneal inflammation. The thickness of the peritoneal membrane is indicated by the distance between the two arrows in each sample shown in FIG. 3. Data are presented as a typical microscopic image of each group. Infiltrates appearing as dark spots in FIG. 3 are polymorphonuclear leukocytes including neutrophils. As examined by histology, similar injury to the peritoneal membrane was noticed in rats after a 4 h-dialysis with hyperosmotic 7.5% or 15% HPG PD solution, indicated by a similar increase in the thickness of the membrane as compared to that of the 0 h control, but the injury was less severe than that in the rats receiving PDS. The thickness of the membrane in the groups receiving a HPG PD solution was only half of that in the PDS group (FIG. 3). When the infiltration of polymorphonuclear leukocytes (i.e. neutrophils) was examined in these stained tissue sections, more polymorphonuclear infiltrates were seen in the peritoneum of rats receiving PDS as compared to those treated with HPG PD solutions, and were positively correlated with more serious membrane injury (FIG. 3).

Figure 4:
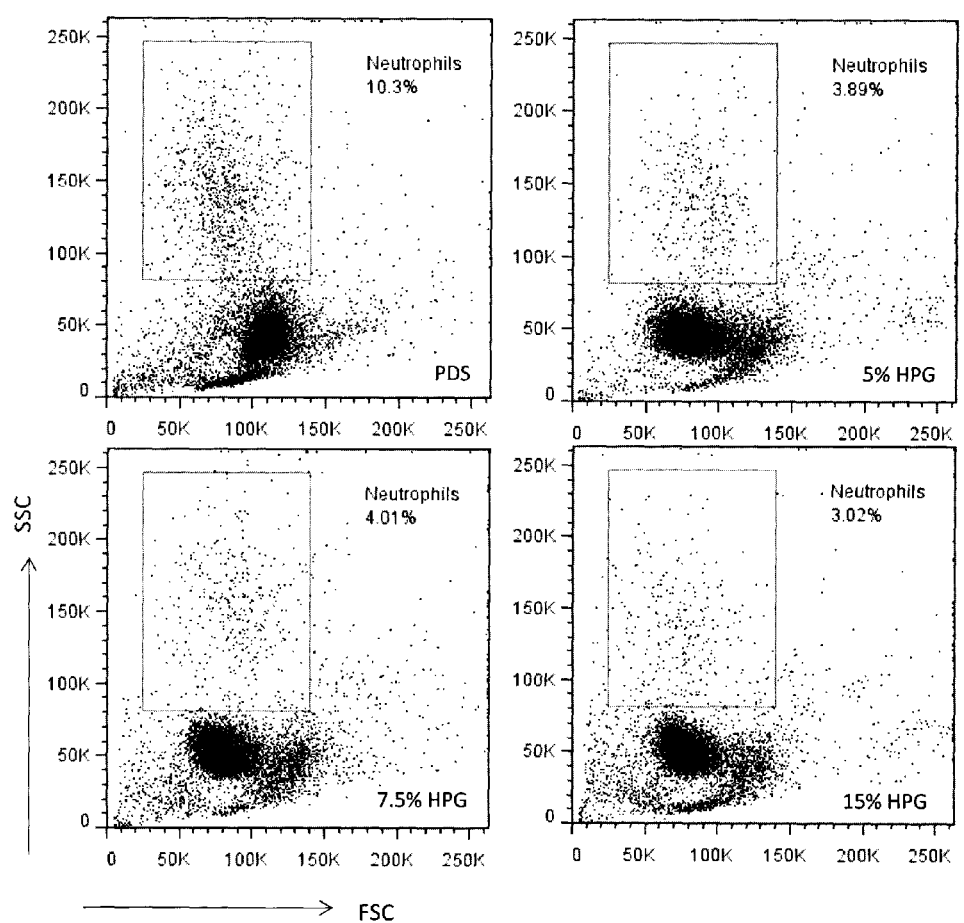
FIG. 4 shows a SCC/FSC plot of percentage of neutrophils in recovered fluid using various HPG PD solutions versus PDS.

To confirm the histological observation, the number of neutrophils and peritoneal mesothelial cells (MCs) in peritoneal effluents was examined by flow cytometric analysis. Flow cytometric analysis was performed on a BD FACSCanto™ II (BD Biosciences, Mississauga, Ontario, Canada). At least 10,000 events were counted for each sample, and data were analyzed with FlowJo software (Tree Star, Ashland, Oreg., USA). For analysis of cell populations in each effluent, approximately one million cells were spun down by centrifugation at 8,000 rpm for 5 minutes, followed by suspending the cells in phosphate-buffered saline (PBS) containing 1% fetal bovine serum (FBS). Neutrophils/granulocytes and monocytes were identified based on their size and granularity in the dot plot of forward scatter (FSC) versus side scatter (SSC) and were counted in the gated area as a percentage of total cell count in the peritoneal effluents. There was no difference in position between the HPG PD solution groups regardless of HPG concentration. As shown in FIG. 4, there were fewer neutrophils in HPG effluents than in PDS effluents, indicated by 3.63±0.87% of neutrophils in accumulated HPG groups (3.43±0.65% in 2.5% HPG; 4.40±1.14% in 5% HPG; 3.43±0.65% in 7.5% HPG; and 3.25±0.74% in 15% HPG, n=4 in each group) compared to 9.31±2.89% in PDS group (n=5) (p<0.0001, HPG vs. PDS). These data were consistent with the presence of more polymorphonuclear infiltrates in the sections of peritoneal tissues of rats dialysed with PDS. The cell volume of macrophage population, determined by the measurement of FSC, in HPG effluents was smaller than in PDS effluents (FIG. 4).

Figure 5:
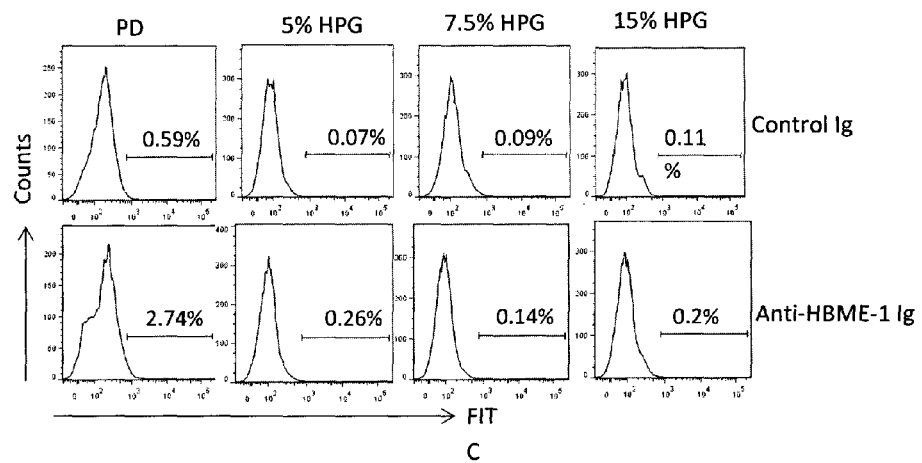
FIG. 5 shows a typical percentage of fluorescein isothiocyanate (FITC) cells in fluorescence-activated cell sorting (FACS) histograms of various HPG PD solutions versus PDS.
Figure 6:
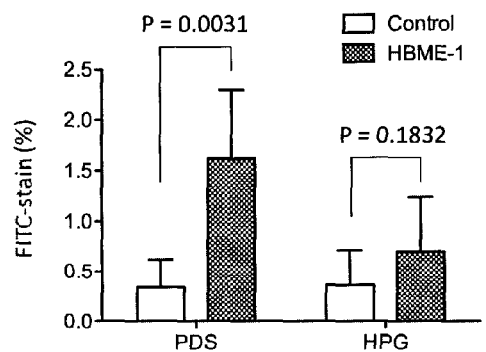
FIG. 6 shows FITC-stained cells in PDS versus accumulated HPG PD solutions.

Peritoneal mesothelial cells (MCs) express a unique cell surface protein, HBME-1, that was used as a marker of peritoneal MCs in the peritoneal effluents. MCs in the cell suspension were identified by fluorescence-activated cell sorting (FACS), a specialized flow cytometric analysis, with rabbit polyclonal anti-HBME-1 antibody conjugated with fluorescein isothiocyanate (FITC) (anti-HBME-1-FITC, Biorbyt Ltd., Riverside, UK) versus rabbit polyclonal anti-mouse IgA-FITC (Cayman Chemical, Ann Arbor, Mich., USA) as a staining control. The cells without antibody stain were used as a negative background for FITC positivity. As shown in FIGS. 5 and 6, there were a significant number of HBME-1-stained cells (1.62±0.68%) as compared to control stain (0.41±0.31%) (p=0.0031, n=4) in the PDS group, while the HBME-1 stain in accumulated HPG solution groups was 0.70±0.54% (the range: 0.24±0.04% to 0.99±0.46%, n=3 in each group), a value that was not significantly higher than the control stain (0.36±0.35%, n=4) (p=0.1832). Data in FIG. 5 is presented as a typical percentage of FITC stained cells in FACS histograms of each group. Data in FIG. 6 is presented as mean±SD of FITC-stained cells in PDS versus accumulated HPG-based solutions, and their differences (control Ig vs. anti-HBME-1 Ig).

Figure 7:
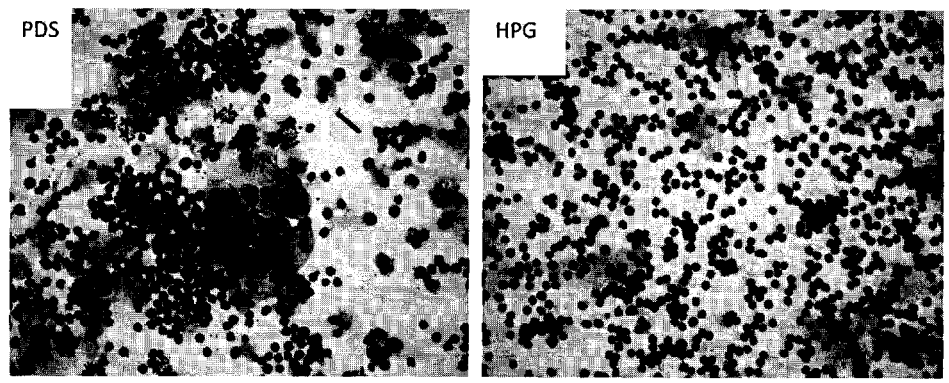
FIG. 7 shows a typical microscopic view of May-Grünwald-Giemsa (MGG)-stained smears of cells in recovered fluid following exposure to a HPG PD solution or PDS.

The presence of MCs in the peritoneal effluents of the PDS group was further confirmed by May-Grünwald-Giemsa (MGG) stain (FIG. 7), evidenced by the presence of MCs in MGG-stained cell smears of peritoneal effluents from the PDS group, but the absence from the HPG PD solution groups. Cells in the peritoneal effluents were spun down by centrifugation at 6,000 rpm for 10 minutes, and were smeared over microscope glass slides. After fully air-drying, cell smears were fixed in methanol. Following rehydration with PBS, the cell smears were stained with May-Grünwald solution (Sigma-Aldrich Canada, Oakville, Ontario, Canada) (1:5 dilution with PBS) for 10 to 15 minutes, washed with PBS and then stained again with Giemsa stain solution (Sigma-Aldrich Canada, Oakville, Ontario, Canada) (1:5 dilution with PBS) for 30 minutes. The color of different types of cells was differentiated by a further wash with PBS. FIG. 7 shows a typical microscopic view of MGG-stained smears of cells in PDS versus HPG (black spots are leukocytes and grey areas are peritoneal MCs). All these data indicate a positive correlation of less peritoneal membrane injury in histology with scarcely detectable presence of detached MCs in the peritoneal effluents following dialysis with HPG PD solutions compared to control PDS. This near-absence of mesothelial detachment indicates that HPG-based solutions are not toxic to the mesothelium in the peritoneal cavity, which strongly reinforces the biocompatibility of polyglycerol. These results also appear to support the understanding that the long-term integrity of the peritoneal membrane may be maintained through the use of polyglycerol as a component of a PD solution.

Example 3: Cell Viability or Tolerance to HPG PD Solutions

Figure 8:
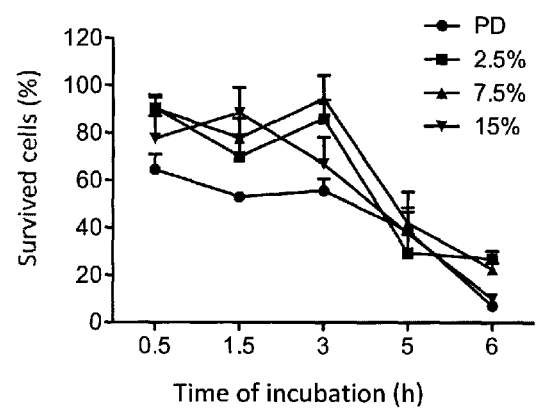
FIG. 8 shows percentage survival of cells versus incubation time in cultured human peritoneal mesothelial cells (HPMCs) following exposure to a HPG PD solution or PDS.
Figure 9:
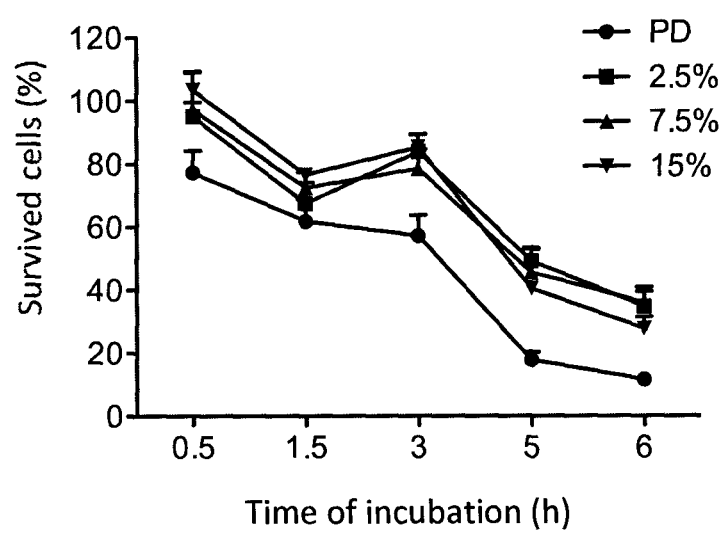
FIG. 9 shows percentage survival of cells versus incubation time in immortalized HPMCs following exposure to a HPG PD solution or PDS.

The cell viability or tolerance to hyperosmotic HPG PD solutions (7.5 and 15%) versus PDS was examined in cultured HPMCs. Primary or immortalized HPMCs (0.2×$10^6$ cells/well) in 24-well plates were grown in K1 culture medium overnight. A confluent monolayer of HPMCs was rinsed with PBS, followed by exposure to HPG PD solution (7.5% or 15% HPG) or PDS at 37° C. under a 5% $CO_2$ atmosphere. Cells were detached by trypin-EDTA solution (Sigma-Aldrich Canada, Oakville, Ontario, Canada), and dead cells were stained positively with Trypan blue. The number of survived or viable cells was counted using a TC10™ automated cell counter (Bio-Rad Laboratories, Mississauga, Ontario, Canada). The percentage of survived cells was calculated as follows: %=($T_x/T_0$)×100, where $T_x$ represents the total number of viable cells at an indicated time point, and $T_0$ indicates the total number of viable cells in an untreated cell monolayer (0 h time point). The number of viable cells in each sample was presented by the average of at least three determinants. As shown in FIG. 8, there were more intact cells, negatively stained by trypan blue, in primary HPMCs following exposure to HPG PD solutions than those to PDS during a 3 h incubation (p<0.0001, 7.5% HPG vs. PDS; p=0.0044, 15% HPG vs. PDS, two-way ANOVA). Similar results were seen in SV40-immortalized HPMCs (p<0.0001, 7.5% HPG vs. PDS, two-way ANOVA; p=0.0067, 15% HPG vs. PDS, two-way ANOVA) (FIG. 9).

Figure 10:
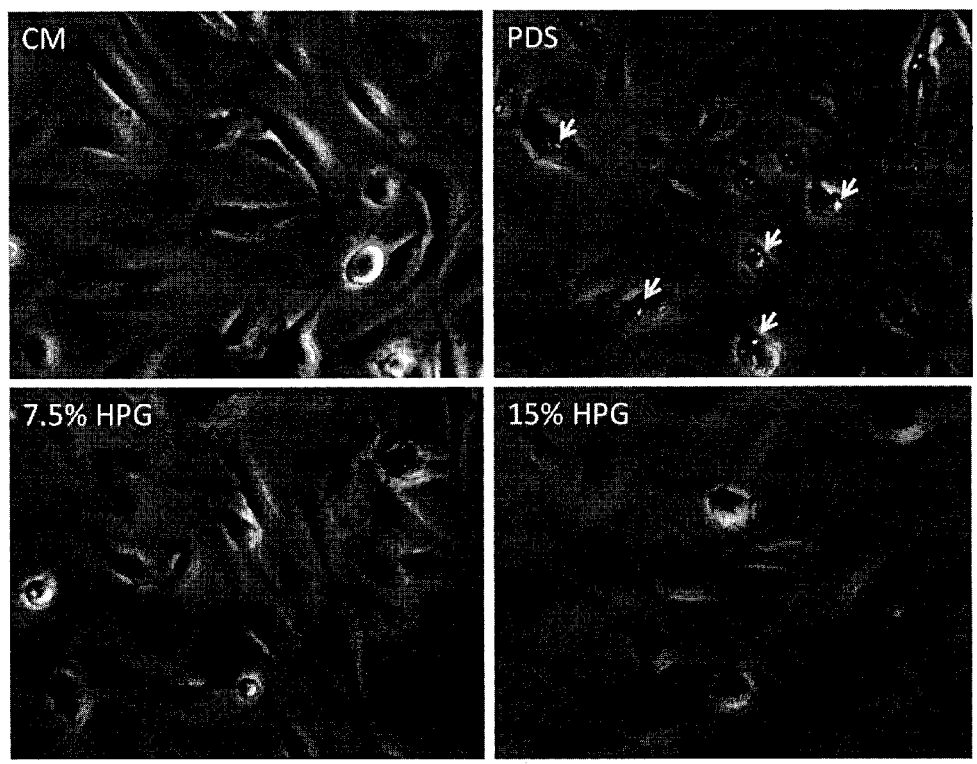
FIG. 10 shows typical microscopic views of immortalized HPMCs after three hours of incubation with culture medium, a HPG PD solution or PDS.

The impact of hyperosmotic HPG solutions versus PDS on the cellular structure of cultured HPMCs was examined under a microscope and using flow cytometric analysis. Immortalized HPMCs (0.2×$10^6$ cells/well) in 24-well plates were grown in K1 culture medium overnight, followed by incubation with K1 culture medium (CM), HPG PD solution (7.5% and 15% HPG) or PDS at 37° C. under 5% $CO_2$ atmosphere. A typical microscopic view of immortalized HPMCs after 3 h of incubation is shown in FIG. 10. As shown in FIG. 10 (by arrows pointing to vacuoles in the cytoplasm), cytoplasmic vacuolation was presented in microscopic views of cultured HPMCs incubated with PDS, but was absent in those cells incubated with HPG solutions or culture medium (CM). This vacuolation is associated with caspase-3-independent cell death and may be associated with glucose cellular uptake when water diffuses out of the cytoplasm to the extracellular medium.

Figure 11:
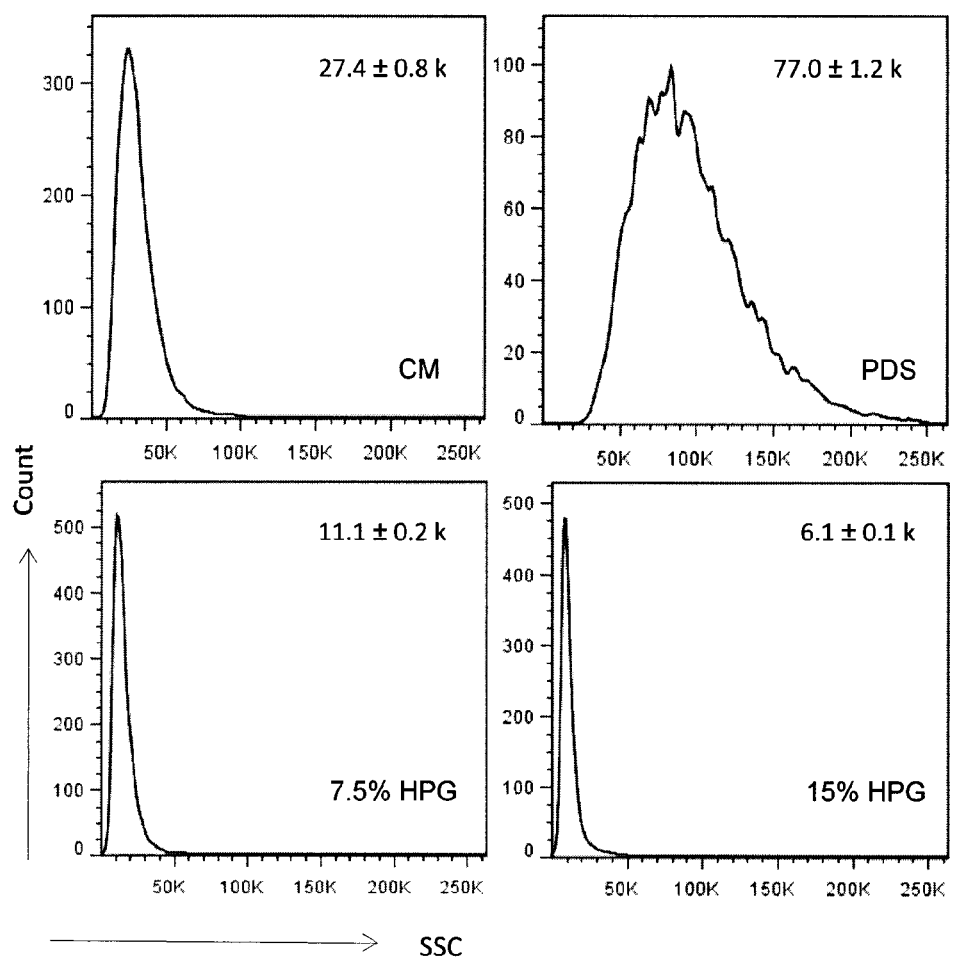
FIG. 11 shows cellular granularity after 30 minutes of incubation with culture medium, a HPG PD solution or PDS.

These results were further confirmed with flow cytometric analysis, in which the measurement of SSC indicated the level of cytoplasmic granularity after 30 minutes of incubation. As shown in FIG. 11, the cytoplasmic granularity of HPMCs was significantly induced by PDS, indicated by an increase in the mean intensity of SSC from 27.4±0.8 (×1000) in the cells with culture medium to 77.0±1.2 (×1000) in those treated with PDS (p<0.0001, t-Test). In contrast to PDS, incubation with HPG PD solutions did not increase the granularity, but it caused a concentration-dependent decrease of SSC measurement, indicated by the fact that the mean intensity of SSC was 11.1±0.2 (×1000) in the cells with 7.5% HPG PD solution, and 6.1±0.1 (×1000) with 15% HPG PD solution (p<0.0001, HPG vs. culture medium, one-way ANOVA).

Figure 12:
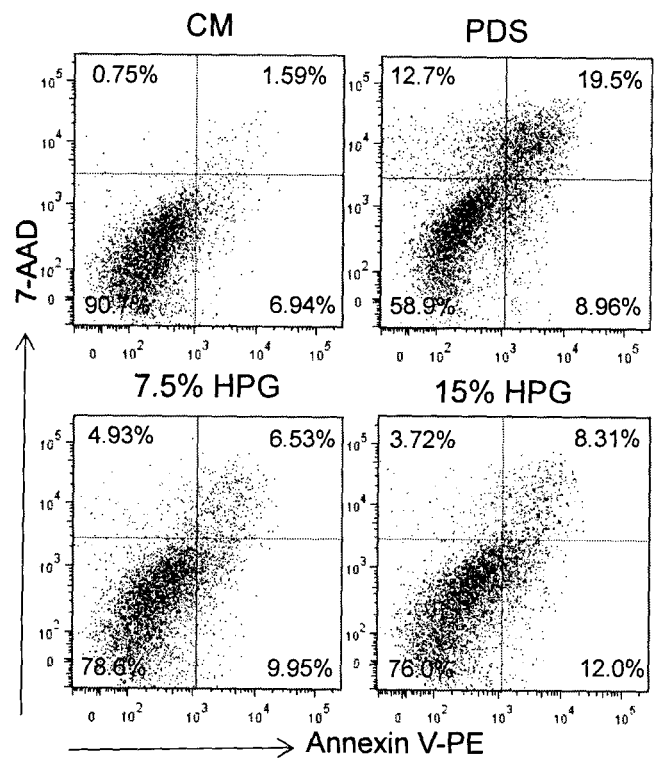
FIG. 12 shows representative FACS plot of cell death after six hours of incubation with culture medium, a HPG PD solution or PDS.

To further verify the beneficial effect of HPG PD solution over PDS on cell survival, cell death or survival was examined during recovery after hyperosmotic stress induced by PDS versus HPG PD solutions using flow cytometric analysis and Western blot. Cell apoptosis or necrosis in HPMCs was measured by FACS analysis following the manufacturer's protocol (BD Biosciences, Mississauga, Ontario, Canada), in which Annexin-V conjugated with phycoerythrin (Annexin-V-PE) staining showed early apoptosis and 7-amino-actinomycin D (7-ADD) staining showed late apoptosis. After incubation with K1 culture medium, a HPG PD solution (7.5% or 15%) or PDS for 1 h, immortalized HPMCs (0.2×$10^6$ cells/well) were recovered in K1 cluture medium. After 6 h of incubation at 37° C. under 5% $CO_2$ atmosphere, cell death was examined by flow cytometric analysis and Western blot analysis. In FIG. 12, non-apoptotic (viable) cells were in the lower left quadrant, necrotic cells were in the upper left quadrant (7-AAD positive only), late apoptotic cells were in the upper right quadrant (both Annexin-V and 7-AAD positive) and early apoptotic cells were in the lower right quadrant (Annexin-V positive only). A single cell suspension of HPMCs was incubated with Annexin-V-PE in 1× binding buffer for 15 minutes, following by staining with 7-AAD. The intensity of fluorescence of apoptotic or necrotic cells was measured as compared to background controls. As shown in FIG. 12 (a representative of a FACS plot of cell death, indicating 7-AAD stained nuclear DNA and Annexin-V stained phospholipids on cell surface) and Table 5, there were more viable or negatively stained cells in HPG PD solution-pretreated cells (75.77±1.35% in 7.5% HPG or 75.27±0.61% in 15% HPG) compared to those (61.7±2.73%) after PDS treatment (p<0.0001). In PDS-pretreated HPMCs, most of the cells died by necrosis or late apoptosis, stained positively with 7-AAD alone or in combination with Annexin-V, as compared to those in culture medium, while cells after incubation with 7.5% or 15% HPG PD solution died mostly in apoptosis, stained positively by Annexin-V alone or in combination with 7-AAD.

Table 5 shows representative data relating to the induction of cell apoptosis by HPG solutions.

TABLE 5

| Stain | CM | 7.5% HPG | 15% HPG | PDS | p values (n = 4) |
|---|---|---|---|---|---|
| 7-AAD$^+$ | 2.98 ± 1.61 | 5.72 ± 0.61 | 4.64 ± 0.74 | 12.90 ± 0.51 | $p < 0.0001$ (PDS vs. CM) |
| | | | | | $p = 0.0178$ (HPG vs. CM) |
| 7-AAD$^+$/Annexin V$^+$ | 3.90 ± 2.55 | 7.13 ± 0.42 | 8.31 ± 0.52 | 17.80 ± 1.81 | $p = 0.0001$ (PDS vs. CM) |
| | | | | | $p = 0.0071$ (HPG vs. CM) |
| Annexin V$^+$ | 7.03 ± 0.08 | 9.52 ± 0.82 | 11.80 ± 1.23 | 7.84 ± 0.85 | $p = 0.1062$ (PDS vs. CM) |
| | | | | | $p < 0.0001$ (HPG vs. CM) |
| Negative stain | 86.07 ± 4.02 | 75.77 ± 1.35 | 75.77 ± 1.35 | 61.70 ± 2.73 | $p < 0.0001$ (PDS vs. 7.5% or 15% HPG) |

Figure 13:
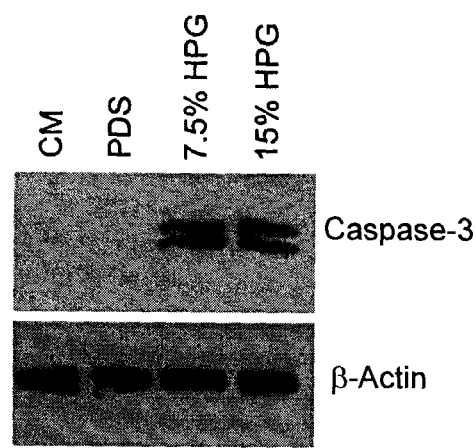
FIG. 13 shows representative Western blots following six hours of incubation with culture medium, a HPG PD solution or PDS.

The apoptosis was further confirmed by the presence of active forms of caspase-3 in cellular protein extracts of HPG PD solution-pretreated HPMCs, but the absence in those of PDS-pretreated cells, in Western blot (FIG. 13). Protein extracts (50-100 μg/sample) were fractionated by 12% SDS-PAGE, then transferred onto a nitrocellulose membrane. Active caspase-3 proteins (17 kDa and 19 kDa) were identified with rabbit polyclonal anti-activated caspase-3 (Asp175) antibody (Cell Signaling Tech, Dancers, Mass., USA) and visualized by an enhanced chemiluminescence assay (ECL, Amersham Pharmacia Biotech, Buckinghamshire, England). Blots were re-probed using anti-actin IgG (Sigma-Aldrich Canada, Oakville, Ontario, Canada) for confirmation of loaded protein in each sample. Taken together, these data might suggest that hyperosmotic HPG PD solutions induce less cell death in apoptosis while PDS induced more cell death that is associated with necrosis and cytoplasmic vacuolation. These results also support the understanding that HPG PD solutions are a promising substitute for glucose-based PD solutions. These data also support the biocompatibility of polyglycerol for use in applications or methods requiring a diffusion and/or osmotic agent.

Example 4: Fluid Removal by Linear Polyglycerol (LPG) in a Rat Model of Peritoneal Dialysis Polyglycerols used in this example were synthesized by anionic ring opening polymerization. In the case of hyperbranched polyglycerols, the polymer was obtained by anionic ring opening multi-branching polymerization of glycidol from tris hydroxymethyl propane (TMP) as initiator using potassium methylate. In the case of linear polyglycerol, ethoxy ethyl glycidyl ether (EEGE) was polymerized via ring opening polymerization from t-BuO$^-$K$^+$ followed by the removal of hydroxyl protecting groups in 35% HCl. Following synthesis, polyglycerols were dialyzed against distilled water and the dialysate was lyophilized to recover the polymer. All the polymers were characterized proton NMR and the molecular weight of the polymers were determined by Multi-angle laser light scattering (Wyatt Technology, Inc, USA).

Four different types of polyglycerols were used as is shown in Table 6. Structures of the polymers are given in FIGS. 1A and 1B. Table 6 shows data relating to the properties of the hyperbranched polglycerol (HPG) and the linear polyglycerol (LPG) used in this study.

TABLE 6

| Sample | $^§$Mn (Da) | $^§$Mw/Mn | Mn ($^1$H NMR) (Da) | Hydrodynamic radius (nm)@ |
|---|---|---|---|---|
| HPG (0.5 kDa) | 480 | 1.32 | 540 | 1.6 m |
| HPG (1.0 kDa) | 820 | 1.34 | 937 | 1.00 |
| HPG (3.0 kDa) | 2700 | 1.26 | 2850 | 0.79 |
| LPG | 2880 | 1.1 | ND | ND |

$^§$Number average molecular weight from GPC-MALLS measurements;
ND—not determined.
@Stoke-Einstein radius from NMR diffusion experiments.

Figure 14:
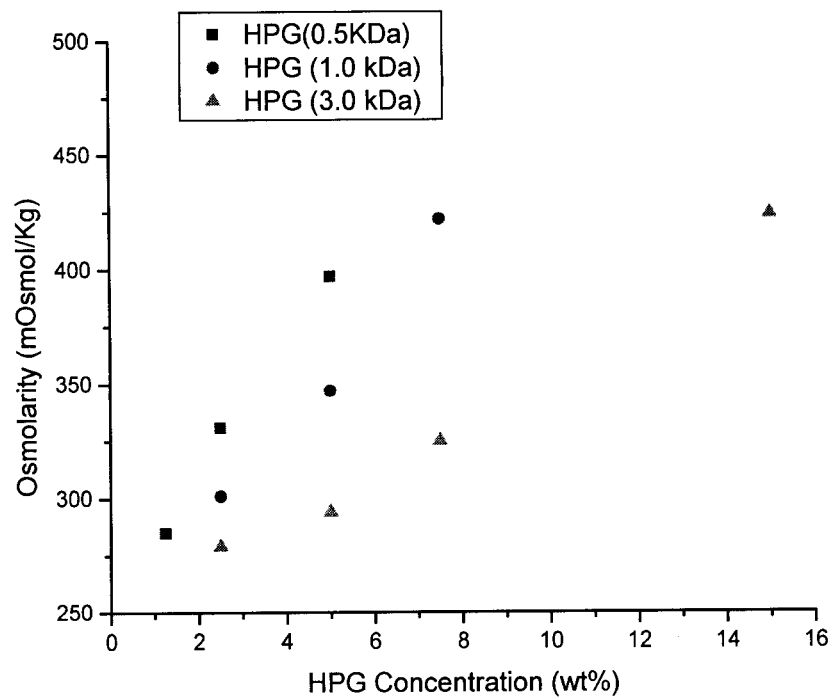
FIG. 14 shows representative data relating to the influence of molecular weight and concentration on osmolarity of a HPG solution.

Polglycerol solutions were prepared at identical salt concentration as that of Dianeal® PD solution. Glucose was replaced with different polyglycerol. The polymer was stirred overnight in buffer and filtered before the measurements. Table 7 shows dependence of polymer molecular weight and concentration on osmolarity$^§$, and FIG. 14 shows the influence of molecular weight and concentration on osmolarity of the HPG solution, with buffer conditions from Table 7.

TABLE 7

| Sample | Concentration (wt %) | Osmolarity (mOsmol/kg) |
|---|---|---|
| HPG (0.5 kDa) | 1.25 | 285 |
| | 2.5 | 331 |
| | 5.0 | 397 |
| | 7.5 | 482 |
| HPG (1.0 kDa) | 2.5 | 301 |
| | 5.0 | 347 |
| | 7.5 | 422 |
| HPG (3.0 kDa) | 2.5 | 279 |
| | 5.0 | 294 |
| | 7.5 | 325 |
| | 15.0 | 424 |

Characteristics of the samples are given in Table 6.
$^§$Buffer compositions (mg/100 mL): Sodium Chloride (NaCl)-538; Sodium Lactate ($C_3H_5NaO_3$)-448; Calcium Chloride (CaCl $2H_2O$)-18.3; Magnesium Chloride ($MgCl_2$ $6H_2O$)-5.08;

LPG PD solution was prepared by dissolving about 7.5 wt % of LPG polymer (Mn-2880 Da) in a solution containing salt at concentrations sodium chloride (538 mg/100 mL), sodium lactate (168 mg/100 mL), calcium chloride dehydrate (18.4 mg/100 mL), magnesium chloride hexahydrate (5.1 mg/100 mL) and sodium bicarbonate (210 mg/100 mL). The pH of the solution was about 7.4. The fluid removal of LPG solution was tested in rat model of peritoneal dialysis. Rats received 30 mL of LPG solution or conventional peritoneal dialysis (PD) solution by intraperitoneal injection. The fluid was recovered at 0 h or 4 h of dwell time. Data were collected from the experiments with 2 rats in each group.

Figure 15:
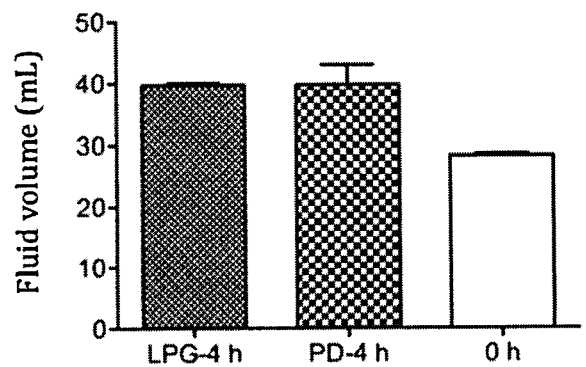
FIG. 15 shows representative data relating to the ultrafiltration (fluid removal) by a LPG PD solution.

After 4 hours of dwell time, LPG solution induced a significantly fluid removal (ultrafiltration) (FIG. 15 shows the ultrafiltration (fluid removal) by LPG PD solution) that is similar to that by the glucose based conventional peritoneal dialysis (PD) solution (Physioneal 40).

Example 5: Removal of Fluid and Urea by Different Sizes of HPG (Buffer Compositions Similar to Dianeal® PD4 CAPD Solution But Without Dextrose)

The different sizes (0.5 and 1 kDa) of HPG (see Table 6 for characteristics) were dissolved in a sterile electrolyte solution (5.38 g/L sodium chloride, 4.48 g/L sodium lactate, 0.183 g/L calcium chloride-dihydrate, and 0.0508 g/L magnesium chloride-hexahydrate, the same composition as in Dianeal® PD4 CAPD solution but without dextrose) at different concentrations. The efficacy of the removal of both fluid and urea of these HPG solutions was tested in rat model of peritoneal dialysis. Rats received 30 mL of HPG solutions or conventional peritoneal dialysis (PDS) (in Dianeal® PD4) solution by intraperitoneal injection. The fluid was recovered at 0 h or 4 h of dwell time. Data were collected from the experiments with 4 rats in each group.

HPG at the size of 0.5 kDa and at the concentrations of 2.5% was equal to the conventional peritoneal dialysis solution (PDS) (Dianeal™ 2.5%) in the fluid removal, and removed significantly more fluid at the higher concentrations (5-7.5%) than that of PDS (Table 3). The total urea removal of these HPG solutions (2.5-7.5%) was similar to that of PDS, but there was a trend of an increase in urea removal following by the increase in HPG concentration in the solution (Table 8 shows the fluid removal/ultrafiltration and urea removal of 0.5 kDa HPG in rats after 4 h of dwell time).

TABLE 8

| Group | Ultrafiltration (mL) | Total urea removal (mmol) |
|---|---|---|
| PDS | 37.23 ± 4.72 | 0.198 ± 0.043 |
| 7.5% HPG (0.5 kDa) | 47.5 ± 3.54 | 0.245 ± 0.035 |
| 5% HPG (0.5 kDa) | 45.5 ± 3.97 | 0.231 ± 0.052 |
| 2.5% HPG (0.5 kDa) | 34.83 ± 1.26 | 0.208 ± 0.047 |
| 1.25% HPG (0.5 kDa) | 27.33 ± 1.53 | 0.163 ± 0.017 |
| P value | P = 0.0148 (7.5% HPG vs. PDS) P = 0.0174 (5% HPG vs. PDS) P = 0.414 (2.5% HPG vs. PDS) | P = 0.1844 (7.5% HPG vs. PDS) P = 0.2949 (5% HPG vs. PDS) P = 0.745 (2.5% HPG vs. PDS) |

Similar results were found in 1 kDa HPG solutions (Table 9) (see Table 6 for characteristics of the polymer). The fluid removal of 5% HPG solution was similar to that of PDS, and was more by 7.5% of HPG solution than that by PDS. The urea removal of these HPG solutions was equal to or higher than that of PDS.

TABLE 9

| Group | Ultrafiltration (mL) | Total urea removal (mmol) |
|---|---|---|
| PDS | 37.23 ± 4.72 | 0.198 ± 0.043 |
| 7.5% HPG (1 kDa) | 44.67 ± 0.58 | 0.268 ± 0.071 |
| 5% HPG (1 kDa) | 39.38 ± 1.25 | 0.206 ± 0.025 |
| 2.5% HPG (1 kDa) | 30.5 ± 0.71 | 0.145 ± 0.029 |
| P value | P = 0.0214 (7.5% HPG vs. PDS) P = 0.3956 (5% HPG vs. PDS) | P = 0.0592 (7.5% HPG vs. PDS) P = 0.7339 (5% HPG vs. PDS) |

Example 6: Removal of Fluid, Urea and Sodium by Different Sizes of HPG (Buffer Compositions Similar to Physioneal 40 Solution but without Dextrose) and Kinetics of Ultrafiltration The different sizes of HPG were dissolved in a sterile electrolyte solution (5.38 g/L sodium chloride, 1.68 g/L sodium lactate, 0.184 g/L calcium chloride-dihydrate, 0.051 g/L magnesium chloride-hexahydrate, and 2.10 g/L sodium bicarbonate, the same composition as in Physioneal 40 solution but without glucose) at different concentrations: 4.8% of 0.5 kDa HPG, 6% of 1 kDa HPG and 14% of 3 kDa HPG. The osmolality of these solutions was 402 mOsm/kg in 0.5 kDa HPG solution, 402 mOsm/kg in 1 kDa HPG solution and 394 mOsm/kg in 3 kDa HPG solution, that was more or less same as in Physioneal 40 solution containing 2.27% of glucose (401 mOsm/kg) (see the characteristics of the HPG in Table 6). All the solutions had pH-7.4. Table 10 shows data relating to osmolarity of HPG and Physioneal 40 PD solutions used for this experiment.

TABLE 10

| PD solutions | Polymer/glucose concentration (wt %) | Osmolarity (mOsmol/kg) |
|---|---|---|
| HPG-0.5 kDa | 4.8 | 402 |
| HPG-1 kDa | 6 | 402 |
| HPG-3 kDa | 14 | 394 |
| Physioneal 40 | 2.27 (glucose) | 401 |

The removal efficacy of fluid, urea and sodium by these HPG solutions versus control Physioneal (2.27% glucose) was tested in a rat model of peritoneal dialysis. Rats received intraperitoneal injection of 30 mL of HPG or Physioneal solution. The fluid/dialysate and serum samples were collected at 0.5, 2, 4 and 8 h of dwell time.

Figure 16:
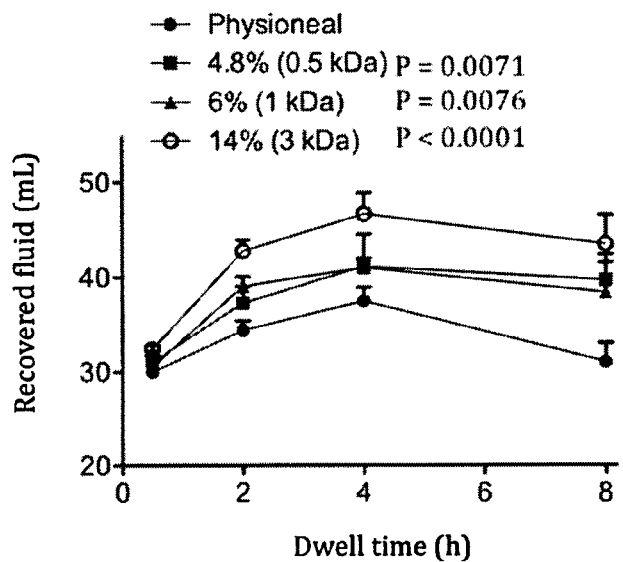
FIG. 16 shows representative data relating to the ultrafiltration of different sizes of HPG as compared to glucose under similar osmolality.

All of HPG solutions removed more fluid compared to Physioneal at all time points under the similar osmolality, and more importantly, the removal efficacy of HPG solutions remained in the prolonged dwell time—8 h, while the conventional Physioneal lost its efficacy. FIG. 16 shows data relating to the ultrafiltration of different sizes of HPG compared to glucose under the similar osmolality. Rats received 30 mL of various HPG solutions or conventional Physioneal 40 (2.27% glucose) solution by intraperitoneal injection. The fluid was recovered at different time points of dwell time. Data were collected from the experiments with 4-5 rats in each group at each time point, and were statistically analyzed by two-way ANOVA.

Figure 17A:
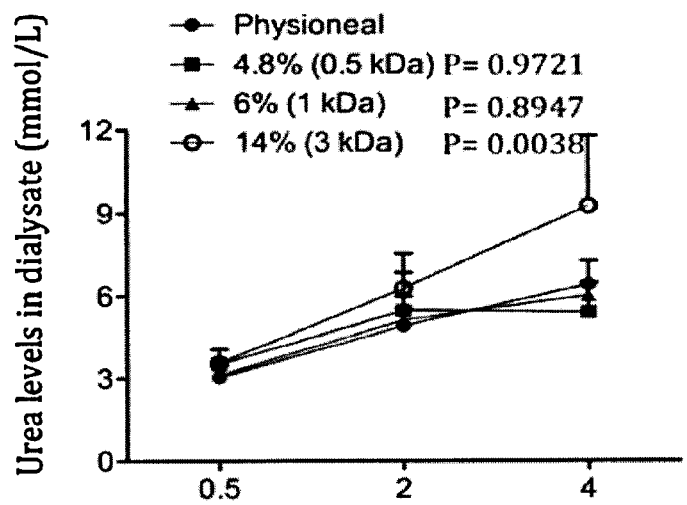
FIGS. 17A-C show representative data relating to the removal of urea by PD solutions comprising different sizes of HPG versus glucose (Physioneal) PD solutions at similar osmolality.
Figure 17B:
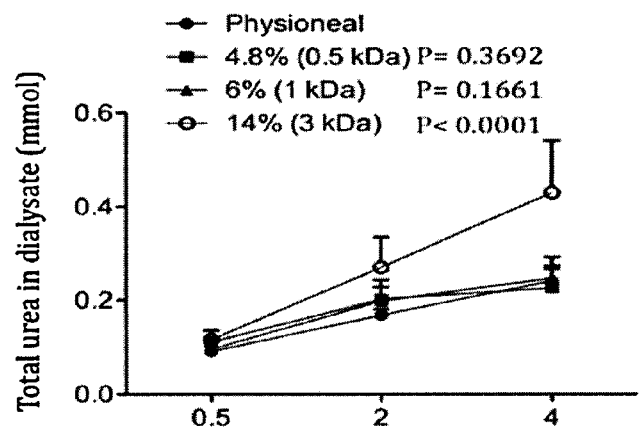
Figure 17C:
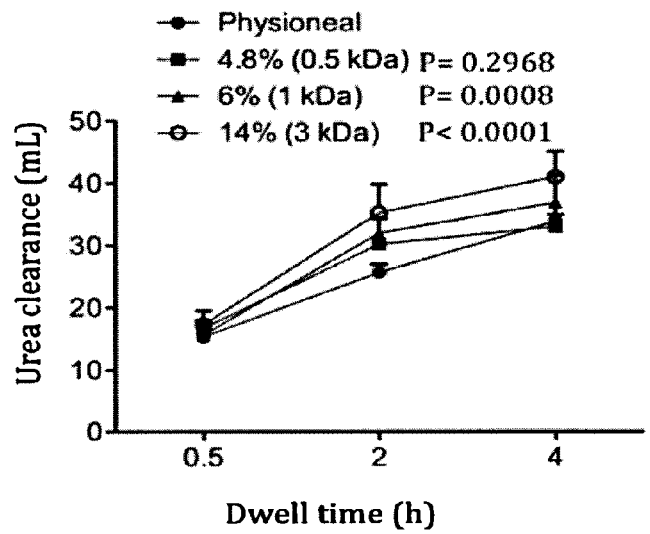

Comparison of urea removal by HPG PD solutions and Physioneal PD solution suggested that the efficacy of 4.8% of 0.5 kDa HPG PD solution was similar to that of Physioneal. Six percent 1 kDa HPG solution had higher urea clearance than Physioneal, and 14% of 3 kDa HPG PD solution removed more urea than Physioneal. FIGS. 17A-C show the urea removal by different sizes HPG PD solution versus glucose (Physioneal) PD solutions at similar osmolality. Rats received 30 mL of various HPG solutions or conventional Physioneal 40 (2.27% glucose) solution by intraperitoneal injection. The fluid was recovered at different time points of dwell time. Data were collected from the experiments with 4-5 rats in each group at each time point, and were statistically analyzed by two-way ANOVA.

Figure 18:
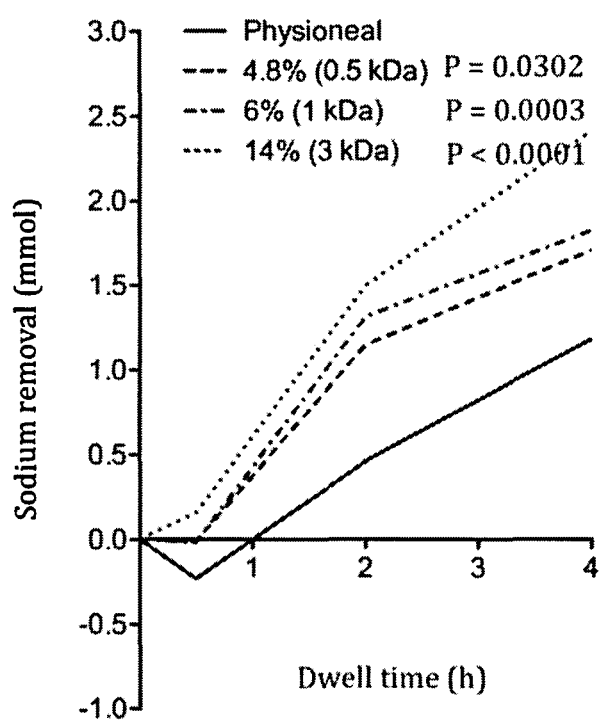
FIG. 18 shows representative data relating to the sodium removal by PD solutions comprising different sizes of HPG versus glucose (Physioneal) PD solutions at similar osmolality.

The sodium removal of HPG PD solutions was compared to Physioneal (FIG. 6). Results showed that Physioneal lost sodium into the body in the beginning and started the sodium removal after 1 h, while there was no sodium loss or removal by 6% of 1 kDa HPG and 4.8% of 0.5 kDa. HPG 14% PD solution (3 kDa) showed increased sodium removal at all the time points compared to Physioneal. FIG. 18 shows the sodium removal by different sizes of HPG versus glucose (Physioneal) PD solutions at similar osmolality. Rats received 30 mL of various HPG solutions or conventional Physioneal 40 (2.27% glucose) solution by intraperitoneal injection. The fluid was recovered at different time points of dwell time. Data are presented as mean of 4-5 rats in each group at each time point, and were statistically analyzed by two-way ANOVA.

Example 7: Biocompatibility of Different Sizes of HPGs Compared to Glucose (Physioneal) at Similar Osmolality The biocompatibility of HPG solutions was compared to Physioneal solution after 4 h of dwell time in a rat model of peritoneal dialysis. First, the biocompatibility was examined by histological analysis.

Figure 19:
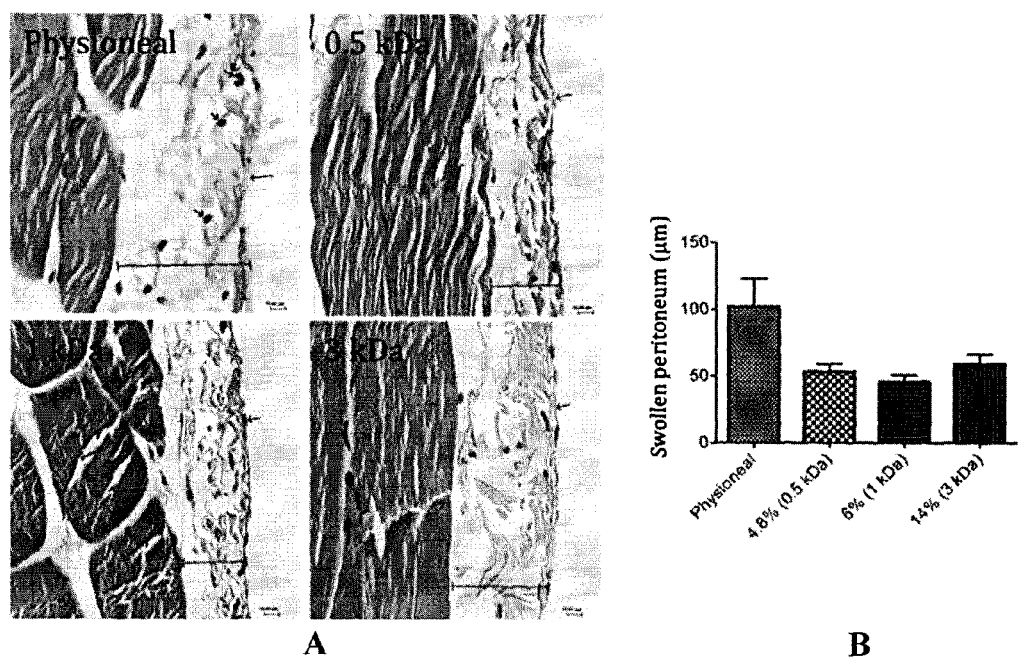
FIG. 19A shows representative images of tissue sections stained with hematoxylin and eosin (H & E)
FIG. 19B shows the corresponding tabulated graph data indicating that the peritoneal membrane was less damaged after exposure to any of HPG solutions versus a Physioneal solution.

FIG. 19 shows images of tissue sections stained hematoxylin and eosin (H & E) and the corresponding tabulated graph data indicating that the peritoneal membrane was less damaged after exposure to any of HPG solutions than that to Physioneal solution. Rats received 30 mL of various HPG solutions or conventional Physioneal 40 (2.27% glucose) solution by intraperitoneal injection. The peritoneal tissues were harvested after 4 h of dwell time. The tissue sections were stained with H&E, and the thickness of the swollen peritoneal membrane was measured using Slidepath Software™. The image was a representative of each group. A long arrow (pointing from left to right) indicates peritoneal mesothelium, a short arrow (pointing from right to left) indicates neutrophils. The graph presents the mean±SEM of swollen peritoneal membrane (indicated by a bar in the image) in each group (n=3-4).

Figure 20:
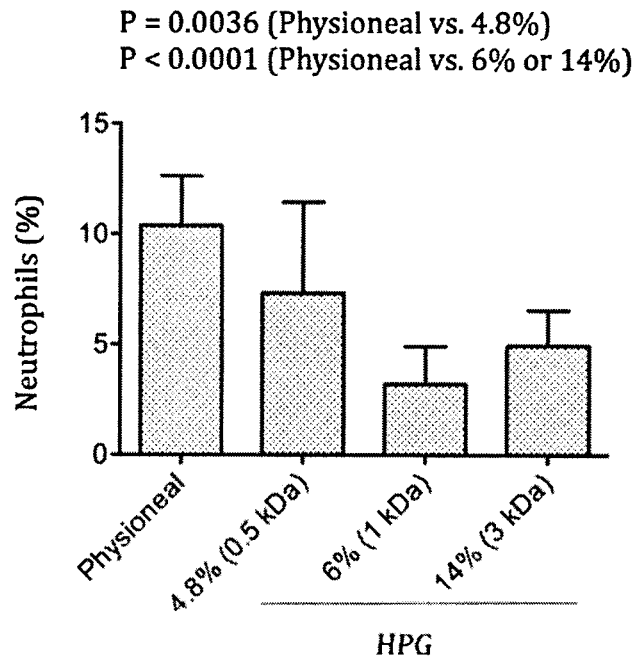
FIG. 20 shows representative data indicating that the percentage of neutrophils in all of the recovered HPG PD solutions was lower than that of the Physioneal solution after four hours of dwell time.

Secondly, the biocompatibility of HPG solutions versus Physioneal solution in peritoneal dialysis was examined by the presence of neutrophils and HBME-1-stained cells (peritoneal mesothelial cells) in dialysate. As shown in FIG. 20, the percentage of neutrophils in all of the recovered HPG PD solutions was lower than that of Physioneal solution after 4 h of dwell time. Rats received 30 mL of various HPG solutions or conventional Physioneal 40 (2.27% glucose) solution by intraperitoneal injection. The dialysates were harvested after 4 h of dwell time. The percentage of neutrophils was counted using a flow cytometry. The data presented the mean±SD of four animals in each group.

Figure 21:
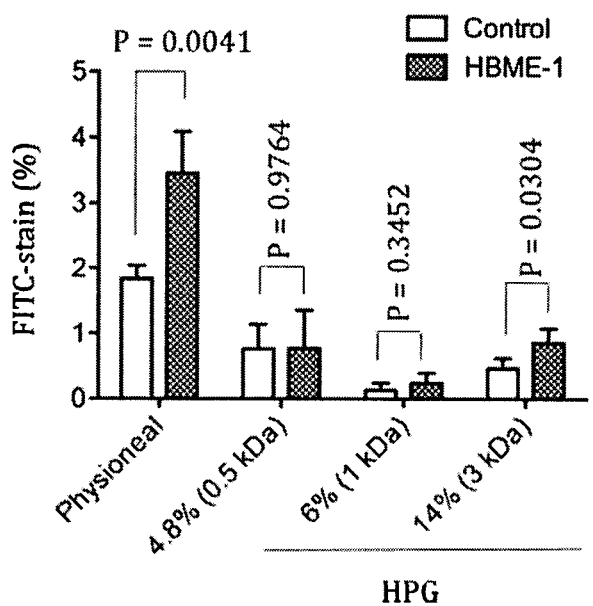
FIG. 21 shows representative data indicating that a significant FITC stain was found in the recovered Physioneal solution, while low detectable levels of FITC stain were seen in any of HPG PD solutions.

The superior biocompatibility of HPG PD solutions versus Physioneal solution in the peritoneal dialysis was also indicated by the less detached peritoneal mesothelial cells, stained positively with anti-HBME-1 antibody conjugated with FITC. FIG. 21 shows that a significant FITC stain was found in the recovered Physioneal solution, while barely detectable levels of FITC stain were seen in any of HPG PD solutions, which indicates less detached peritoneal mesothelial cells in the dialysate after dialysis with HPG solutions compared to that with Physioneal solution. Rats received 30 mL of various HPG PD solutions or conventional Physioneal 40 (2.27% glucose) solution by intraperitoneal injection. The dialysates were harvested after 4 h of dwell time. The mesothelial cells were stained with anti-HBME-1 antibody conjugated with FITC, and were counted using a flow cytometry. The data presented the mean±SD of four animals in each group. Control samples were stained with a control antibody conjugated with FITC.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as any open-ended term, substantially equivalent to the phrase "including, but not limited to", and the words "comprise" and "comprises" have a corresponding meaning. As used herein, the singular forms "a", "an" and "the" include plural referents unless the context clearly dictates otherwise. Thus, for example, reference to "a thing" includes more than one such thing.

Citation of references herein is not an admission that such references are prior art to the present invention nor does it constitute any admission as to the contents or date of these documents.

What is claimed is:

1. A peritoneal dialysis solution, comprising:
   (a) a polyglycerol, wherein the polyglycerol is of a molecular weight between about 0.15 kDa and about 10 kDa, the degree of branching of the polyglycerol is greater than 0 to about 1.0, and the polyglycerol comprises about 0.30% by weight to about 35% by weight of the peritoneal dialysis solution;
   (b) sodium;
   (c) calcium;
   (d) magnesium; and
   (e) water.

2. The peritoneal dialysis solution of claim 1 wherein the polyglycerol is of a molecular weight between about 0.45 kDa and about 3.0 kDa.

3. The peritoneal dialysis solution of claim 1 wherein the pH of the peritoneal dialysis solution is between about 4.0 and about 8.0.

4. The peritoneal dialysis solution of claim 3 wherein the pH of the peritoneal dialysis solution is between about 6.5 and about 7.5.

5. The peritoneal dialysis solution of claim 1 wherein the polyglycerol comprises about 1.25% by weight to about 20% by weight of the peritoneal dialysis solution.

6. The peritoneal dialysis solution of claim 1 wherein the peritoneal dialysis solution has an osmolarity between about 200 milliosmols per liter and about 600 milliosmols per liter.

7. The peritoneal dialysis solution of claim 1 wherein the polyglycerol has a polydispersity of about 1.0 to about 5.0.

8. The peritoneal dialysis solution of claim 1 wherein the polyglycerol is dendritic.

9. The peritoneal dialysis solution of claim 1 wherein the degree of branching of the polyglycerol is between about 0.4 and about 0.7.

10. The peritoneal dialysis solution of claim 1 wherein the degree of branching of the polyglycerol is between about 0.7 and about 1.0.

11. The peritoneal dialysis solution of claim 1 wherein the polyglycerol further comprises one or more hydrophobic groups, hydrophilic groups or both.

12. The peritoneal dialysis solution of claim 11 wherein the one or more hydrophobic groups, hydrophilic groups or both are joined to from about 1% to about 40% of hydroxyl groups on the polyglycerol.

13. The peritoneal dialysis solution of claim 11 wherein the one or more hydrophobic groups, hydrophilic groups or both comprise one or more of a carboxylic acid, an amine, a substituted amine, a quaternary amine, an amino acid, a phosphate, a sulfate, a sulfonate, a phosphonate, an alkyl, an alkene, an alkyne, an alkyl ether, an aromatic, an aromatic ether, a zwitterionic group, a carbohydrate, a disulfide, a ketal, a substituted ketal, an acetal, a substituted acetal, an ester group, a thioester, a urethane, an ester-amide, an amide group, a peptide, a phenol, a halogen, or a thiol.

14. The peritoneal dialysis solution of claim 1 further comprising one or more electrolytes, one or more amino acids, one or more diffusion agents, one or more osmotic agents, or a combination thereof.

15. The peritoneal dialysis solution of claim 14 wherein the osmotic agent or diffusion agent comprises chloride, lactate, bicarbonate, a bicarbonate producing agent, potassium, dextrose, fructose, glycerol, sorbitol, manitol, L-carnitine, bovine serum albumin (BSA), maltose, maltotriose, maltopentose, xylitol, synthetic polymer or natural polymer.

16. A kit for formulating a peritoneal dialysis solution, the kit comprising:
(a) a polyglycerol, wherein the polyglycerol is of a molecular weight between about 0.15 kDa and about 10 kDa, the degree of branching of the polyglycerol is greater than 0 to about 1.0, and the polyglycerol comprises about 0.30% by weight to about 35% by weight of the peritoneal dialysis solution;
(b) sodium;
(c) calcium;
(d) magnesium; and
(e) instructions for using the polyglycerol, sodium, calcium, and magnesium for formulating the peritoneal dialysis solution.

17. The peritoneal dialysis solution of claim 1 wherein the degree of branching of the polyglycerol is greater than 0 to about 0.4.

18. The peritoneal dialysis solution of claim 1 wherein the polyglycerol is hyperbranched.

19. The peritoneal dialysis solution of claim 6 wherein the peritoneal dialysis solution has an osmolarity between about 260 milliosmols per liter and about 520 milliosmols per liter.

20. The peritoneal dialysis solution of claim 19 wherein the peritoneal dialysis solution has an osmolarity between about 280 milliosmols per liter and about 450 milliosmols per liter.

21. The peritoneal dialysis solution of claim 7 wherein the polyglycerol has a polydispersity of about 1.0 to about 2.0.

22. The peritoneal dialysis solution of claim 21 wherein the polyglycerol has a polydispersity of about 1.0 to about 1.5.

23. The peritoneal dialysis solution of claim 1 further comprising lactate.

24. The peritoneal dialysis solution of claim 1 wherein the peritoneal dialysis solution does not comprise glucose.

25. The peritoneal dialysis solution of claim 1 wherein:
the pH of the peritoneal dialysis solution is between about 6.5 and about 7.5;
the polyglycerol is of a molecular weight between about 0.15 kDa and about 4.0 kDa;
the polyglycerol comprises about 1.25% by weight to about 20% by weight of the peritoneal dialysis solution;
the peritoneal dialysis solution has an osmolarity between about 280 milliosmols per liter and about 450 milliosmols per liter; and
the polyglycerol has a polydispersity of about 1.0 to about 5.0.

26. The peritoneal dialysis solution of claim 1 wherein:
the pH of the peritoneal dialysis solution is between about 6.5 and about 7.5;
the polyglycerol is of a molecular weight between about 0.15 kDa and about 4.0 kDa;
the polyglycerol comprises about 1.25% by weight to about 20% by weight of the peritoneal dialysis solution;
the peritoneal dialysis solution has an osmolarity between about 280 milliosmols per liter and about 450 milliosmols per liter;
the concentration of sodium in the peritoneal dialysis solution is about 131 mEq/L; and
the polyglycerol has a polydispersity of about 1.0 to about 5.0.

27. The peritoneal dialysis solution of claim 1 wherein:
the peritoneal dialysis solution further comprises lactate;
the pH of the peritoneal dialysis solution is between about 6.5 and about 7.5;
the polyglycerol is of a molecular weight between about 0.15 kDa and about 4.0 kDa;
the polyglycerol comprises about 1.25% by weight to about 20% by weight of the peritoneal dialysis solution;
the peritoneal dialysis solution has an osmolarity between about 280 milliosmols per liter and about 450 milliosmols per liter; and
the polyglycerol has a polydispersity of about 1.0 to about 5.0.

28. The kit of claim 16, wherein the polyglycerol has a polydispersity of about 1.0 to about 5.0.

29. The kit of claim 16, whereby the concentration of sodium in the peritoneal dialysis solution is about 131 mEq/L.

30. The kit of claim 16, whereby the concentration of calcium in the peritoneal dialysis solution is about 2.3 mEq/L.

31. The kit of claim 16, whereby the concentration of magnesium in the peritoneal dialysis solution is about 0.5 mEq/L.

32. The kit of claim 16, wherein the degree of branching of the polyglycerol is greater than 0 to about 0.4.

33. The kit of claim 16, wherein the degree of branching of the polyglycerol is between about 0.4 and about 0.7.

34. The kit of claim 16, wherein the degree of branching of the polyglycerol is between about 0.7 and about 1.0.

35. The kit of claim 16, wherein the polyglycerol is of a molecular weight between about 0.15 kDa and about 5.0 kDa.

36. The kit of claim 16, wherein the polyglycerol is of a molecular weight between about 0.15 kDa and about 4.0 kDa.

37. The kit of claim 16, wherein the polyglycerol is of a molecular weight between about 0.45 kDa and about 4.0 kDa.

38. The kit of claim 16, whereby the polyglycerol comprises about 1.25% by weight to about 20% by weight of the peritoneal dialysis solution.

39. The kit of claim 16, whereby the polyglycerol comprises about 2.5% by weight to about 15% by weight of the peritoneal dialysis solution.

40. The kit of claim 16, whereby the polyglycerol comprises about 2.5% by weight to about 5% by weight of the peritoneal dialysis solution.

41. The kit of claim 16, whereby the polyglycerol comprises about 5% by weight to about 7.5% by weight of the peritoneal dialysis solution.

42. The kit of claim 16, whereby the polyglycerol comprises about 6% by weight to about 14% by weight of the peritoneal dialysis solution.

43. The kit of claim 16, wherein the kit further comprises water.

44. The kit of claim 16, wherein the kit further comprises chloride.

45. The kit of claim 44, whereby the concentration of chloride in the peritoneal dialysis solution is about 97 mEq/L.

46. The kit of claim 16, wherein the kit further comprises lactate.

47. The kit of claim 46, whereby the concentration of lactate in the peritoneal dialysis solution is about 40 mEq/L.

48. The kit of claim 16, wherein the kit further comprises bicarbonate.

49. The kit of claim 16, whereby the pH of the peritoneal dialysis solution is between about 6.5 and about 7.5.

50. The kit of claim 16, whereby the peritoneal dialysis solution has an osmolarity between about 200 milliosmols per liter and about 600 milliosmols per liter.

51. The peritoneal dialysis solution of claim 1 wherein the concentration of sodium in the peritoneal dialysis solution is about 131 mEq/L.

52. The peritoneal dialysis solution of claim 1 wherein the concentration of calcium in the peritoneal dialysis solution is about 2.3 mEq/L.

53. The peritoneal dialysis solution of claim 1 wherein the concentration of magnesium in the peritoneal dialysis solution is about 0.5 mEq/L.

54. The peritoneal dialysis solution of claim 1 wherein the polyglycerol is of a molecular weight between about 0.15 kDa and about 5.0 kDa.

55. The peritoneal dialysis solution of claim 1 wherein the polyglycerol is of a molecular weight between about 0.15 kDa and about 4.0 kDa.

56. The peritoneal dialysis solution of claim 1 wherein the polyglycerol is of a molecular weight between about 0.15 kDa and about 3.0 kDa.

57. The peritoneal dialysis solution of claim 1 wherein the polyglycerol is of a molecular weight between about 0.45 kDa and about 4.0 kDa.

58. The peritoneal dialysis solution of claim 1 wherein the polyglycerol comprises about 2.5% by weight to about 15% by weight of the peritoneal dialysis solution.

59. The peritoneal dialysis solution of claim 1 wherein the polyglycerol comprises about 2.5% by weight to about 5% by weight of the peritoneal dialysis solution.

60. The peritoneal dialysis solution of claim 1 wherein the polyglycerol comprises about 5% by weight to about 7.5% by weight of the peritoneal dialysis solution.

61. The peritoneal dialysis solution of claim 1 wherein the polyglycerol comprises about 7.5% by weight to about 15% by weight of the peritoneal dialysis solution.

62. The peritoneal dialysis solution of claim 1 wherein the polyglycerol comprises about 6% by weight to about 14% by weight of the peritoneal dialysis solution.

63. The peritoneal dialysis solution of claim 1, further comprising chloride.

64. The peritoneal dialysis solution of claim 63 wherein the concentration of chloride in the peritoneal dialysis solution is about 97 mEq/L.

65. The peritoneal dialysis solution of claim 23 wherein the concentration of lactate in the peritoneal dialysis solution is about 40 mEq/L.

66. The peritoneal dialysis solution of claim 1, further comprising bicarbonate.

67. The peritoneal dialysis solution of claim 1, further comprising one or more amino acids.

68. The peritoneal dialysis solution of claim 1 wherein the peritoneal dialysis solution does not comprise a carbohydrate.

69. The peritoneal dialysis solution of claim 25 wherein the polyglycerol comprises about 2.5% by weight to about 15% by weight of the peritoneal dialysis solution.

70. The peritoneal dialysis solution of claim 26 wherein the polyglycerol comprises about 2.5% by weight to about 15% by weight of the peritoneal dialysis solution.

71. The peritoneal dialysis solution of claim 27 wherein the polyglycerol comprises about 2.5% by weight to about 15% by weight of the peritoneal dialysis solution.

72. The peritoneal dialysis solution of claim 25 wherein the degree of branching of the polyglycerol is between about 0.4 and about 0.7.

73. The peritoneal dialysis solution of claim 26 wherein the degree of branching of the polyglycerol is between about 0.4 and about 0.7.

74. The peritoneal dialysis solution of claim 27 wherein the degree of branching of the polyglycerol is between about 0.4 and about 0.7.

75. The kit of claim 16, wherein the pH of the peritoneal dialysis solution is between about 4.0 and about 8.0.

76. The kit of claim 50, wherein the peritoneal dialysis solution has an osmolarity between about 260 milliosmols per liter and about 520 milliosmols per liter.

77. The kit of claim 76, wherein the peritoneal dialysis solution has an osmolarity between about 280 milliosmols per liter and about 450 milliosmols per liter.

* * * * *